(12) United States Patent
Erikson et al.

(10) Patent No.: US 6,858,390 B2
(45) Date of Patent: *Feb. 22, 2005

(54) APTAMERS CONTAINING SEQUENCES OF NUCLEIC ACID OR NUCLEIC ACID ANALOGUES BOUND HOMOLOGOUSLY, OR IN NOVEL COMPLEXES

(75) Inventors: Glen H. Erikson, Providenciales (TC); Jasmine I. Daksis, Richmond Hill (CA)

(73) Assignee: Ingeneus Corporation, Bridgetown (BB)

( * ) Notice: Subject to any disclaimer, the term of this patent is extended or adjusted under 35 U.S.C. 154(b) by 163 days.

This patent is subject to a terminal disclaimer.

(21) Appl. No.: 09/961,865

(22) Filed: Sep. 24, 2001

(65) Prior Publication Data

US 2003/0022853 A1 Jan. 30, 2003

Related U.S. Application Data

(63) Continuation-in-part of application No. 09/224,505, filed on Dec. 31, 1998, now Pat. No. 6,294,333, said application No. 09/961,865, and a continuation-in-part of application No. 09/909,496, filed on Jul. 20, 2001, which is a continuation-in-part of application No. 09/664,827, filed on Sep. 19, 2000, said application No. 09/961,865, and a continuation-in-part of application No. 09/613,263, filed on Jul. 10, 2000, now Pat. No. 6,420,115, which is a continuation-in-part of application No. 09/468,679, filed on Dec. 21, 1999, now Pat. No. 6,403,313.

(51) Int. Cl.[7] .......................... C12Q 1/68; C12P 19/34; C12M 1/34; C07H 21/02; C07H 21/04
(52) U.S. Cl. .......................... 435/6; 435/7.1; 435/91.1; 435/91.2; 435/5; 435/287.2; 536/22.1; 536/23.1; 536/24.3; 536/24.31; 536/24.32; 536/24.33
(58) Field of Search ...................... 435/5, 6, 7.1, 91.1, 435/91.2, 287.2; 536/22.1, 23.1, 24.3–24.33

(56) References Cited

U.S. PATENT DOCUMENTS

| | | |
|---|---|---|
| 4,220,450 A | 9/1980 | Maggio |
| 4,235,869 A | 11/1980 | Schwarzberg |
| 4,876,187 A | 10/1989 | Duck et al. |
| 4,963,477 A | 10/1990 | Tchen |
| 5,011,769 A | 4/1991 | Duck et al. |

(List continued on next page.)

FOREIGN PATENT DOCUMENTS

| | | |
|---|---|---|
| EP | 1092777 A1 | 4/2001 |
| GB | 2333359 A | 7/1999 |
| GB | 2338301 A | 12/1999 |
| WO | WO 97/45539 A1 | 12/1997 |
| WO | WO 00/20633 A1 | 4/2000 |

OTHER PUBLICATIONS

Webster New Riverside Dictionary 1994 g. 237.*
ABSTRACT of JP 5237000, Yoshitami (Sep. 17, 1993).

(List continued on next page.)

*Primary Examiner*—Jeffrey Siew
(74) *Attorney, Agent, or Firm*—Caesar, Rivise, Bernstein, Cohen & Pokotilow, Ltd.

(57) ABSTRACT

An aptamer contains at least two parallel or antiparallel heteropolymeric nucleobase-containing sequences bonded together by Watson-Crick complementary base interaction or by homologous base interaction, provided that: (a) when the aptamer is single-stranded, the at least two sequences are bonded together by homologous base interaction; and (b) when the aptamer is a duplex and the at least two sequences are antiparallel to each other, the at least two sequences are bonded together by homologous base interaction. The aptamer can be used to bind ligands or to catalyze reactions when functioning as an aptazyme.

17 Claims, 8 Drawing Sheets

Wildtype c-JUN:wildtype JD1F/2F binding

U.S. PATENT DOCUMENTS

| | | | |
|---|---|---|---|
| 5,332,659 | A | 7/1994 | Kidwell |
| 5,403,711 | A | 4/1995 | Walder et al. |
| 5,538,848 | A | 7/1996 | Livak et al. |
| 5,539,082 | A | 7/1996 | Nielsen et al. |
| 5,558,998 | A | 9/1996 | Hammond et al. |
| 5,567,588 | A | 10/1996 | Gold et al. |
| 5,660,988 | A | 8/1997 | Duck et al. |
| 5,705,346 | A | 1/1998 | Okamoto et al. |
| 5,707,801 | A | 1/1998 | Bresser et al. |
| 5,712,128 | A | 1/1998 | Been et al. |
| 5,720,928 | A | 2/1998 | Schwartz |
| 5,731,146 | A | 3/1998 | Duck et al. |
| 5,800,984 | A | 9/1998 | Vary |
| 5,800,992 | A | 9/1998 | Fodor et al. |
| 5,814,447 | A | 9/1998 | Ishiguro et al. |
| 5,814,516 | A | 9/1998 | Vo-Dinh |
| 5,824,477 | A | 10/1998 | Stanley |
| 5,824,557 | A | 10/1998 | Burke et al. |
| 5,840,867 | A | 11/1998 | Toole |
| 5,846,729 | A | 12/1998 | Wu et al. |
| 5,858,774 | A | 1/1999 | Malbon et al. |
| 5,861,124 | A | 1/1999 | Hosoi et al. |
| 5,874,555 | A | 2/1999 | Dervan et al. |
| 5,888,739 | A | 3/1999 | Pitner et al. |
| 5,912,332 | A | 6/1999 | Agrawal et al. |
| 5,948,897 | A | 9/1999 | Sen et al. |
| 5,985,620 | A | 11/1999 | Sioud |
| 6,001,657 | A * | 12/1999 | Hardin et al. ............... 436/501 |
| 6,013,442 | A | 1/2000 | Kolesar et al. |
| 6,017,709 | A | 1/2000 | Hardin et al. |
| 6,027,880 | A | 2/2000 | Cronin et al. |
| 6,046,004 | A | 4/2000 | Wu et al. |
| 6,048,690 | A | 4/2000 | Heller et al. |
| 6,060,242 | A | 5/2000 | Nie et al. |
| 6,107,078 | A | 8/2000 | Keese et al. |
| 6,117,657 | A | 9/2000 | Usman et al. |
| 6,147,198 | A | 11/2000 | Schwartz |
| 6,207,388 | B1 | 3/2001 | Grossman |
| 6,251,591 | B1 | 6/2001 | Wu et al. |
| 6,255,050 | B1 | 7/2001 | Nie et al. |
| 6,255,469 | B1 | 7/2001 | Seeman et al. |
| 6,265,170 | B1 | 7/2001 | Picard et al. |
| 6,287,765 | B1 * | 9/2001 | Cubicciotti .................... 435/6 |
| 6,287,772 | B1 | 9/2001 | Stefano et al. |
| 6,294,333 | B1 | 9/2001 | Daksis et al. |
| 6,312,925 | B1 | 11/2001 | Meyer, Jr. et al. |
| 2002/0037506 | A1 * | 3/2002 | Lin et al. ........................ 435/6 |

OTHER PUBLICATIONS

Baran et al., *Nucleic Acids Research* 25:297–303 (1997).
Bohmann et al., *Science*, 238:1386–1392 (Dec. 1987).
Carlsson et al., 380 *Nature* 207 (Mar. 21, 1996).
Chan et al., *J. Mol. Med.* 75 Issue 4:267–282 (1997).
Dalrymple et al., *Nucleic Acids Research*, vol. 13, No. 21, pp. 7865–7879 (1985).
Davis, "Kinetic Characterization of Thrombin–Aptamer Interactions" *Pharmacia Biosensor Application Note 305* (1994).
Dohoney et al., *Nature*, 409(6818): 370–374 (Jan. 18, 2001) (Abstract).
Durland et al., *Biochemistry*, 30:9246–9255 (1991).
Egholm et al., 365 *Nature* 566 (Oct. 7, 1993).
Fernandez et al., "Pulling on Hair(pins)," 292 *Science* 653 (Apr. 27, 2001).
Floris et al., 260 *Eur. J. Biochem.* 801–809 (1999).
Hill et al., *Methods in Enzymology*, 278:390–416 (1997).
Johansen and Jacobsen, *J Biomol Struct Dyn*, 16(2):205–22 (Oct. 1998) (Abstract).
Kadonaga et al., *Cell*, 51:1079–1090 (Dec. 24, 1987).
Korth et al., "Prion (PrPSc)–Specific Epitope Defined by a Monoclonal Antibody," *Nature* 390:74–77 (1997) (Abstract).
Kukreti et al., 25 *Nucleic Acids Research* 4264–4270 (1997).
Marsh et al., *Nucleic Acids Research*, 23:696–700 (1995).
Marsh et al., *Biochemistry* 33:10718–10724 (1994).
Marshall et al., "A biopolymer by any other name would bind as well: a comparison of the ligand–binding pockets of nucleic acids and proteins," 5(6) *Structure* 729–734 (1997).
Mazumder et al., *Biochemistry* 35:13762–13771 (1996).
Sen et al., *Nature* 334:364–366 (Jul. 28, 1988).
Sen et al., *Biochemistry* 31:65–70 (1992).
Sturm et al., *Genes & Development*, 2:1582–1599 (1988).
Tomac et al., 118 *J. Am. Chem. Soc.* 5544–5552 (1996).
U.S. Appl. No. 09/344,525, Daksis et al.
U.S. Appl. No. 09/713,177, Erikson et al.
U.S. Appl. No. 09/885,731, Erikson et al.
U.S. Appl. No. 09/911,047, Erikson et al.
Watson, James, "A Personal Account of the Discovery of the Structure of DNA," (1968).
Williamson et al., *Cell* 59:871–880 (Dec. 1, 1989).
Wilson et al., *Cell*, 74:115–125 (Jul. 16, 1993).
Zhurkin et al., *J. Mol. Biol.*, vol. 239, 181–200 (1994).
Rocher, Christophe et al., *Nucleic Acids Research*, "Initiation of DNA replication by DNA polymerases from primers forming a triple helix," 2001, vol. 29, No. 16, 3320–3326.
Nielsen et al., *Bioorganic & Medicinal Chemistry*, "Strand Displacement Recognition of Mixed Adenine–Cytosine Sequences in Double Stranded DNA by Thymine–Guanine PNA (Peptide Nucleic Acid)", 2429–2434, 9 (2001).

* cited by examiner

SEQUENCE LISTING

```
<160> NUMBER OF SEQ ID NOS: 22

<210> SEQ ID NO 1
<211> LENGTH: 17
<212> TYPE: DNA
<213> ORGANISM: Human

<400> SEQUENCE: 1
gtgtctgact catgctt                                                17

<210> SEQ ID NO 2
<211> LENGTH: 17
<212> TYPE: DNA
<213> ORGANISM: Human

<400> SEQUENCE: 2
aagcatgagt cagacac                                                17

<210> SEQ ID NO 3
<211> LENGTH: 17
<212> TYPE: DNA
<213> ORGANISM: Human

<400> SEQUENCE: 3
gtgtcttact catgctt                                                17
```

```
<210> SEQ ID NO 4
<211> LENGTH: 17
<212> TYPE: DNA
<213> ORGANISM: Human

<400> SEQUENCE: 4
aagcatgagt aagacac                                                    17

<210> SEQ ID NO 5
<211> LENGTH: 132
<212> TYPE: PRT
<213> ORGANISM: Human

<400> SEQUENCE: 5
```

Gln Pro Gln Gln Gln Gln Pro Pro His His Leu Pro Gln Gln Met
 1               5                  10                  15

Pro Val Gln His Pro Arg Leu Gln Ala Leu Lys Glu Glu Pro Gln Thr
                20                  25                  30

Val Pro Glu Met Pro Gly Glu Thr Pro Pro Leu Ser Pro Ile Asp Met
            35                  40                  45

Glu Ser Gln Glu Arg Ile Lys Ala Glu Arg Lys Arg Met Arg Asn Arg
    50                  55                  60

Ile Ala Ala Ser Lys Cys Arg Lys Arg Lys Leu Glu Arg Ile Ala Arg
65                  70                  75                  80

Leu Glu Glu Lys Val Lys Thr Leu Lys Ala Gln Asn Ser Glu Leu Ala
                85                  90                  95

Ser Thr Ala Asn Met Leu Arg Glu Gln Val Ala Gln Leu Lys Gln Lys
            100                 105                 110

Val Met Asn His Val Asn Ser Gly Cys Gln Leu Met Leu Thr Gln Gln
        115                 120                 125

Leu Gln Thr Phe
    130

```
<210> SEQ ID NO 6
<211> LENGTH: 132
<212> TYPE: PRT
<213> ORGANISM: Human

<400> SEQUENCE: 6
```

Gln Pro Gln Gln Gln Gln Pro Pro His His Leu Pro Gln Gln Met
 1               5                  10                  15

Pro Val Gln His Pro Arg Leu Gln Ala Leu Lys Glu Glu Pro Gln Thr
                20                  25                  30

Val Pro Glu Met Pro Gly Glu Thr Pro Pro Leu Ser Pro Ile Asp Met
            35                  40                  45

Glu Ser Gln Glu Arg Ile Lys Ala Glu Arg Lys Arg Met Arg Asn Arg
    50                  55                  60

Ile Ala Ala Ser Ile Asp Arg Lys Arg Lys Leu Glu Arg Ile Ala Arg
65                  70                  75                  80

Leu Glu Glu Lys Val Lys Thr Leu Lys Ala Gln Asn Ser Glu Leu Ala
                85                  90                  95

Ser Thr Ala Asn Met Leu Arg Glu Gln Val Ala Gln Leu Lys Gln Lys
            100                 105                 110

Val Met Asn His Val Asn Ser Gly Cys Gln Leu Met Leu Thr Gln Gln
        115                 120                 125

Leu Gln Thr Phe
    130

```
<210> SEQ ID NO 7
<211> LENGTH: 20
<212> TYPE: DNA
<213> ORGANISM: Human

<400> SEQUENCE: 7
ccggccgggg cgggcttttt                                                   20

<210> SEQ ID NO 8
<211> LENGTH: 20
<212> TYPE: DNA
<213> ORGANISM: Human

<400> SEQUENCE: 8
aaaagccccg ccccggccgg                                                   20

<210> SEQ ID NO 9
<211> LENGTH: 20
<212> TYPE: DNA
<213> ORGANISM: Human

<400> SEQUENCE: 9
ccggcctaaa tagggctttt                                                   20

<210> SEQ ID NO 10
<211> LENGTH: 20
<212> TYPE: DNA
<213> ORGANISM: Human

<400> SEQUENCE: 10
aaaagcccta tttaggccgg                                                   20

<210> SEQ ID NO 11
<211> LENGTH: 18
<212> TYPE: DNA
<213> ORGANISM: Human

<400> SEQUENCE: 11
gagtatgcaa atcatgtg                                                     18

<210> SEQ ID NO 12
<211> LENGTH: 18
<212> TYPE: DNA
<213> ORGANISM: Human

<400> SEQUENCE: 12
cacatgattt gcatactc                                                     18

<210> SEQ ID NO 13
<211> LENGTH: 18
<212> TYPE: DNA
<213> ORGANISM: Human

<400> SEQUENCE: 13
gagtcggcac ctcatgtg                                                     18

<210> SEQ ID NO 14
<211> LENGTH: 18
<212> TYPE: DNA
<213> ORGANISM: Human

<400> SEQUENCE: 14
cacatgaggt gccgactc                                                     18
```

```
<210> SEQ ID NO 15
<211> LENGTH: 20
<212> TYPE: DNA
<213> ORGANISM: Herpes Simplex Virus Type I

<400> SEQUENCE: 15
ggcggtaatg agatacgagc                                                    20

<210> SEQ ID NO 16
<211> LENGTH: 20
<212> TYPE: DNA
<213> ORGANISM: Herpes Simplex Virus Type I

<400> SEQUENCE: 16
gctcgtatct cattaccgcc                                                    20

<210> SEQ ID NO 17
<211> LENGTH: 20
<212> TYPE: DNA
<213> ORGANISM: Herpes Simplex Virus Type I

<400> SEQUENCE: 17
ggcggtcctg agcgacgagc                                                    20

<210> SEQ ID NO 18
<211> LENGTH: 20
<212> TYPE: DNA
<213> ORGANISM: Herpes Simplex Virus Type I

<400> SEQUENCE: 18
gctcgtcgct caggaccgcc                                                    20

<210> SEQ ID NO 19
<211> LENGTH: 23
<212> TYPE: DNA
<213> ORGANISM: Herpes Simplex Virus Type I

<400> SEQUENCE: 19
gtgcatgcta atgatattct ttg                                                23

<210> SEQ ID NO 20
<211> LENGTH: 23
<212> TYPE: DNA
<213> ORGANISM: Herpes Simplex Virus Type I

<400> SEQUENCE: 20
caaagaatat cattagcatg cac                                                23

<210> SEQ ID NO 21
<211> LENGTH: 23
<212> TYPE: DNA
<213> ORGANISM: Herpes Simplex Virus Type I

<400> SEQUENCE: 21
gtgccggctc ctgatcgtct ttg                                                23

<210> SEQ ID NO 22
<211> LENGTH: 23
<212> TYPE: DNA
<213> ORGANISM: Herpes Simplex Virus Type I

<400> SEQUENCE: 22
caaagacgat caggagccgg cac                                                23
```

APTAMERS CONTAINING SEQUENCES OF NUCLEIC ACID OR NUCLEIC ACID ANALOGUES BOUND HOMOLOGOUSLY, OR IN NOVEL COMPLEXES

CROSS-REFERENCE TO RELATED APPLICATIONS

This application is a continuation-in-part of U.S. patent application No. 09/224,505, filed Dec. 31, 1998 now U.S. Pat. No. 6,294,333. This application is also a continuation-in-part of U.S. patent application Ser. No. 09/909,496, filed Jul. 20, 2001, which is a continuation-in-part of Ser. No. 09/664,827, filed Sep. 19, 2000. This application is also a continuation-in-part of U.S. patent application Ser. No. 09/613,263, filed Jul. 10, 2000, now U.S. Pat. No. 6,420,115, which is a continuation-in-part of U.S. patent application Ser. No. 09/468,679, filed Dec. 21, 1999 now U.S. Pat. No. 6,403,313. The disclosures of the foregoing patent applications are incorporated by reference herein in their entireties.

SPECIFICATION

BACKGROUND OF THE INVENTION

1. Field of Invention

The invention relates to aptamers, and more particularly to aptamers comprising at least two nucleobase-containing sequences, which are parallel or antiparallel to each other, and bound by Watson-Crick or homologous binding preferences.

2. Description of Related Art

Protein-nucleic acid complexes are known to play an important role in a variety of biological processes. See, e.g., Hill et al. "Fluorescence Approaches to Study of Protein-Nucleic Acid Complexation," 278 Methods in Enzymology 390 (1997). For example, DNA-binding proteins are known to play an important role in gene regulation. Genes are typically regulated at the transcriptional level by DNA-binding proteins, which are referred to as transcription factors. Transcription factors regulate gene expression by specifically binding to a target nucleic acid sequence in promoter DNA.

Due to the biological importance of protein-nucleic acid interaction, a variety of methods for studying protein-nucleic acid binding characteristics have been proposed. See, e.g., Hill et al. and the references cited therein. See also, the inventors' prior U.S. patent application Ser. No. 09/224, 505.

Aptamers can be designed to interact specifically with non-nucleic acid substances, such as proteins or other bodily substances. Aptamers can function as high affinity receptors for small molecule ligands or can tightly interact with target proteins for therapeutic or diagnostic purposes. The folding of an initially unstructured molecule around its ligand and forming a hydrogen-bond network with its ligand facilitate this binding. Marshall et al. "A biopolymer by any other name would bind as well: a comparison of the ligand-binding pockets of nucleic acids and proteins." 5(6) Structure 729–734 (1997). These aptamers can be ligands used to screen for other molecules or they can be catalytic. Aptamers that are catalytic are considered approximate ribozymes, or aptazymes. To date, aptamers have been almost exclusively of single-stranded RNA. Aptamers can as well be designed to interact specifically with nucleic acid substances, other than to simply bind them on the basis of Watson-Crick base pairing between bases in nucleic acid sequences of opposite orientation. Such aptamers, if catalytic, may be fairly called aptazymes. Such specific action can be sought for therapeutic or diagnostic purposes.

A small number of RNA molecules are known to be active as catalysts and do not merely serve as the means by which information is moved out of the nucleus. Ribozymes can be self-cleaving or can cleave other RNA. This activity is understood to be dependent on the RNA's secondary structure, which can be dependent on factors such as base sequence and the inclusion of metallocations. In the past, there has been a large effort directed at building novel or improved ribozymes. Ribozymes have great utility in artificially controlling gene expression. Developers have sought to take advantage of the very specific charge patterns of nucleic acids, their bases and backbones and DNA's ability to form predictable secondary structure, based upon base sequence and predictable Watson-Crick base pairing. Nucleic acid's small dimensions and flexible nature make it well suited for constructing complexes capable of recognizing and specifically binding to features on other substances, such as proteins, and perhaps thereupon adopting tertiary structure.

Through SELEX-driven screening (U.S. Pat. No. 5,567, 588 to Gold et al.), which depends upon binding to single-stranded nucleic acids mounted on biochips, researchers have discovered ribozymes, which are 100 or even 1000 fold more active catalytically.

Fernandez et al. "Pulling on Hair(pins)," 292 Science 653. (Apr. 27, 2001), reports data collected from a single molecule conformational change in a ribozyme. Fernandez et al. also reports that such essentially duplex nucleic acid structures undergo "all or none" discrete transitions in conformation, not the progressive pair by pair binding one would expect.

Researchers have disclosed a circular RNA that has enzymatic activity to cleave a separate RNA molecule at a cleavage site and RNA molecules capable of conferring stability to RNA in vivo through an endogenous ribozyme binding protein. See U.S. Pat. No. 5,712,128 to Been et al. and U.S. Pat. No. 5,985,620 to Sioud.

U.S. Pat. No. 5,840,867 to Toole discloses methods for making aptamers and aptamers that bind to biomolecules. These aptamers can be used to interfere with the normal biological function of the biomolecules, as a separation tool, a diagnostic or a therapeutic. The aptamers can be single chain or duplex RNA or DNA. However, this patent only discloses intramolecular or intermolecular Watson-Crick binding of the antiparallel variety.

Researchers have applied single-stranded RNA aptamers directed against Syrian golden hamster prion protein and the aptamers were able to recognize their specific target within a mixture of hundreds of different proteins contained in tissue homogenates thereby tending to validate the utility of aptamers. Korth et al. "Prion (PrPSc)-specific epitope defined by a monoclonal antibody." Nature 390:74–77 (1997).

U.S. Pat. No. 6,207,388 to Grossman is directed to methods, compositions, kits and apparatus to identify and detect the presence or absence of target analytes. The compositions comprise an RNA molecule that can be an aptamer that binds to a target molecule. However, Grossman only teaches Watson-Crick antiparallel binding of nucleobases.

U.S. Pat. No. 5,858,774 to Malbon et al. provides a method of regulating a gene by introducing into a cell an antisense DNA construct. However, this patent does not teach using a nucleic acid to bind to a non-nucleic acid.

Aptamers have been used to identify and evaluate new substances, or drugs, that have a specific binding activity, or that predictably alter the binding characteristics of other binding pairs/complexes. For example, researchers have found a single-stranded DNA aptamer that binds the active site of thrombin, (a protein involved in blood coagulation), and exhibits anti-coagulation effects in vivo. Davis, "Kinetic characterization of Thrombin-Aptamer interactions." Pharmacia Biosensor Application Note 305, 1994.

Despite the foregoing developments, there is still room in the art for aptamers of novel design with unique binding properties, and for novel uses of such aptamers.

BRIEF SUMMARY OF THE INVENTION

The invention provides an aptamer comprising at least two parallel or antiparallel heteropolymeric nucleobase-containing sequences bonded together by Watson-Crick complementary base interaction or by homologous base interaction, provided that: (a) when said aptamer is single-stranded, said at least two sequences are bonded together by homologous base interaction; and (b) when said aptamer is a duplex and said at least two sequences are antiparallel to each other, said at least two sequences are bonded together by homologous base interaction.

Also provided is a method for binding a ligand. The method comprises contacting the ligand with an aptamer of the invention.

Still further provided is a method for catalyzing a reaction with a catalytic aptamer (aptazyme) of the invention.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1A:
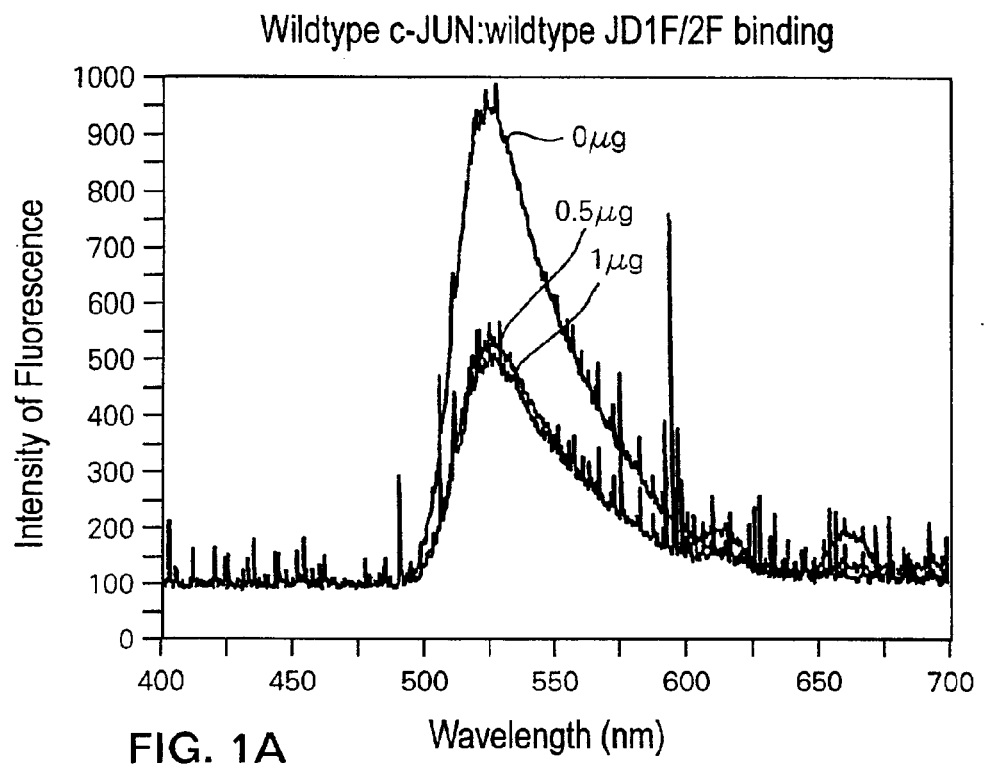
FIGS. 1A, 1B, 1C, 1D, 2A, 2B, 3A, 3B, 4A, 4B, 5A, 5B, 6A, 6B, 7A and 7B are fluorescent spectra.

The invention flows from our elucidation of the specific binding properties of heteropolymeric nucleobase sequences. Our prior patent applications disclosed the specific binding of a heteropolymeric strand to duplex nucleic acid and the specific binding of duplex nucleic acid to other duplex nucleic acid. Our prior patent applications have also disclosed that heteropolymeric sequences of nucleobases (and/or their analogues) can specifically bind to each other by homologous base bonding as well as by Watson-Crick base interaction, and that such specific base bonding is not limited to sequences on strands having antiparallel directionality relative to each other or to duplex formation. Thus, heteropolymeric base sequences (and/or their analogues) can specifically bind to each other with parallel or antiparallel directionality, wherein the bases bond by homologous base bonding and/or Watson-Crick base bonding rules, whether present on the same nucleic acid strand or on different strands.

The invention is more than merely the disclosure of unorthodox, but specific, binding properties of nucleic acids. The invention encompasses novel aptamers, methods for making the aptamers, and methods for using the aptamers for therapeutic, diagnostic, prophylactic, engineering or other purposes.

Aptamers are nucleic acids typically designed to bind specifically with non-nucleic acid substances, such as proteins or other biomolecules (e.g., carbohydrates, lipids, etc.) although they may also bind nucleic acids for certain purposes. The term "aptazymes" as used herein means an aptamer catalyst. Aptazymes can specifically bind to nucleic acids (particularly to catalyze cleavage thereof), as well as to proteins and other biomolecules. "Binding" in terms of aptamer and target as used herein refers to an interaction or complexation between a target and an aptamer, resulting in a sufficiently stable complex so as accomplish a therapeutic purpose or to permit detection of the complexes or separation of aptamer:target complexes from uncomplexed structures under given conditions. Aptamers can perform many of the same functions as protein molecules, including undergoing specific changes in their 2 or 3-dimensional structure in response to ligand-binding. Aptamers can be functionalized by including unpaired nucleobases or non-nucleobase molecules.

We disclose aptamers that employ our discovery that mixed nucleobase sequences can bind specifically in either the Watson-Crick complementary binding motif or in the homologous binding motif. Our previous elucidation of the mixed nucleobase sequence triplex and quadruplex demonstrate that the specificity of nucleobase binding is not restricted to a specific plane or surface of the nucleobase, and that a nucleobase is capable of binding specifically to two or more nucleobases at one time, and, most remarkably, that a nucleobase can bind one nucleobase in the Watson-Crick complementary manner while specifically binding complementarily or homologously to another nucleobase. All of these discoveries make possible a great expansion of aptamer design.

Without wishing to be bound to any particular theory, we believe that nucleobase sequences are inherently ambivalent as to binding motif and that binding is a function of the opportunities to bind presented by their environment.

We believe as well that binding motif specificity is a property of a sequence of bases which is enforced upon nucleation having been achieved. Accordingly, we believe the binding preference of a nucleated strand is the result of base stacking, electrostatic forces or the like operating within the strand of nucleobases. Once such a motif preference has been established for a strand, it was possible to observe Markovian "all or none kinetics" in connection with the forced disassociation of the bound bases and their "two-state" reassociation which does not exhibit the expected step-wise sequential "zipping up" of the re-annealing bases. We propose that the behavior observed by Fernandez, supra, is the product of "motif preference" or "motif memory" by the nucleobase strand. Fernandez suggests experiments examining refolding by the autonomous units of proteins will be carried out soon. Similar "memory" may be observed as regards refolding protein.

We further believe it useful to connect binding motif preference and the phenomenon of mismatch instability. We are much impressed by the great instability introduced locally by an incompatible pair of nucleobases, even nucleobases whose geometry suggests they ought not be destabilizing to their bound neighbors. We connect this instability with contradiction of the imperative inherent in the motif preference of the bound sequences.

We find it useful to connect binding motif preference to certain facts relating to protein-DNA interaction, such as translation by Rec BCD along duplex DNA. Dohoney, Nature 2001 Jan 18; 409(6818): 370–374, reports the protein's movement and attendant DNA unwinding at a constant and exceptionally fast velocity. We imagine that duplex DNA stability can be undermined in an allosteric manner, just as we imagine that nucleation is allosteric and creates or enforces a binding preference on adjacent sequences of nucleobases.

Our prior applications have shown that motif preference can result in homologous binding, which is specific between mixed base sequences on antiparallel strands. As backbone deformation, which was previously condsidered to be a barrier to such pairing, is an unlikely concomitant of such binding, it is likely that unexpected facts will be learned when such duplexes are observed by NMR scanning or other techniques.

Our prior applications have also shown that parallel strands of mixed sequence nucleobases can bind specifically under either motif to form a duplex or that parallel or antiparallel mixed base sequences can bind specifically to previously formed duplex. Most remarkably, we have shown that duplex-bound bases remain reactive specifically as regards other proximal duplex-bound bases, either pursuant to the Watson-Crick complementary binding motif or the Homologous binding motif. Accordingly, our inventions relating to aptamers depend upon our many remarkable discoveries relating to nucleic acid binding, behavior and characteristics, which can greatly extend the field of aptamer design and use.

It is not surprising that complementary base pairing in duplex DNA as suggested by Watson and Crick in 1953 should have carried all before it when proposed and greatly inhibited thinking and experimentation about nucleic acid binding.

In 1940 Linus Pauling and Max Delbruck had expressed the view that molecular complementarity was the basis of biological specificity and the "secret of life". The views of the paper, The Nature of Intermolecular Forces Operative in Biological Processes" prepared the ground for the expectation that such complementary binding would be by different moieties and not by the same moieties. Hence, the readiness of Watson and Crick and others to discard the concept of homologous binding by nucleic acids.

Nucleic acid strands have inherent directionality. The conventional wisdom holds that strands of opposite directionality, i.e., which are antiparallel in their orientation to one another, can form a duplex through Watson-Crick complementary binding of their respective base sequences.

Certain duplex aptamers according to the invention, on the other hand, comprise two strands of nucleic acid (and/or nucleic acid analogues) hybridized in parallel relation to one another, wherein specific binding is either through homologous base pairing or Watson-Crick base pairing. Conventional wisdom holds that such duplexes do not exist, or at least would be extremely unstable due to, e.g., backbone irregularities necessitated by the conformational requirements of parallel base bonding. Even more surprising is our discovery that under appropriate mild hybridization conditions, parallel homologous duplex bonding demonstrates specificity and stability rivaling or exceeding that of Watson-Crick complementary antiparallel duplex.

The invention also encompasses duplex aptamers containing two strands of nucleic acid (and/or nucleic acid analogues) hybridized in antiparallel relation to one another, wherein specific binding, remarkably, is through homologous base pairing.

As used herein, the terms "Watson-Crick base pairing", "complementary base pairing" and the like are intended to define specific association between opposing or adjacent pairs of nucleic acid and/or nucleic acid analogue strands via matched bases (e.g., A:T; G:C and/or A:U). In the context of the "non-canonical" complexes described herein, including parallel duplexes, parallel and antiparallel triplexes, and parallel quadruplexes, terms like "Watson-Crick base bonding" and "complementary base bonding" are intended to denote bonding between A and T, A and U and/or G and C, but not necessarily in the edgewise, opposed planar conformation first suggested by Watson and Crick.

In addition to the conventional binding motif first proposed by Watson and Crick (the "W-C motif"), and conformational variants thereof encompassed by the foregoing definition of Watson-Crick base bonding, the present invention encompasses aptamers formed by homologous base bonding. In homologous base bonding, bases bond specifically with identical bases rather than complementary bases but not necessarily in a manner similar to the edgewise opposed planar conformation first suggested by Watson and Crick. Thus, in the "Homologous motif", homologous base pairs include A:A, G:G, C:C, T:T and U:U. References to either binding "motif" comprise not only specific binding by nucleobases opposite one another which interact edgewise, as in an antiparallel Watson-Crick bound duplex, but also nucleobases in sequences which are sufficiently proximal to one another whether stably bound in antiparallel duplexes or not. A nucleobase can specifically bind a base previously bound in a duplex in accordance with the Watson-Crick motif and simultaneously, bind a second nucleobase on the basis of the Homologous motif.

The binding by the bases of nucleic acid strands is affected or conditioned by a number of factors, particularly the binding potential of the strands pursuant to either the W-C motif or Homologous motif, and ionic conditions (e.g., salt concentration and/or type). Salty conditions tend to favor the formation of Watson-Crick bonding over homologous bonding. Homologous motif quadruplexes are favored over W-C motif quadruplexes under identical buffer conditions probably because the localized environment can become relatively low-salt, based on the presence of the charged backbones of the two duplex nucleic acids.

An aptamer of the invention can comprise one or more sequences of nucleobases and/or nucleobase analogues, provided the nucleobases are related to the nucleobases to which they are to specifically bind by either the W-C motif or the Homologous motif. Contrary to certain teachings of the prior art, the binding nucleobases of the aptamer need not be homopolymeric to achieve binding, in the case of triplex or quadruplex formation. Thus, in certain embodiments, the nucleobases of a first binding sequence are arranged in a heteropolymeric sequence of interspersed purines and pyrimidines, and the nucleobases of a second, binding sequence are arranged in a heteropolymeric sequence of interspersed purines and pyrimidines, and are at least partially complementary or partially homologous to the first sequence. For example, the binding sequence of a strand can contain 25% to 75% purine bases and 75% to 25% pyrimidine bases in any order. Aptamers of the invention can form from heteropolymeric sequences, which as defined herein, means sequences containing at least one purine nucleobase or purine analogue and at least one pyrimidine nucleobase or pyrimidine analogue in at least their binding segments. Heteropolymeric sequences preferably lack homopolymeric fragments greater than 5 bases long. Other nucleobases are also suitable for use in the invention, such as, e.g., synthetic analogues of naturally occurring bases which have specific Watson-Crick and/or homologous binding affinities to other bases.

In addition to self-binding nucleic acids and duplexes based on homologous binding, aptamers of the invention also include triplex and quadruplex nucleic acids wherein opposing heteropolymeric strands are linked by Watson-Crick complementary bases or by homologous bases, and the relative directionality of the bound sequences is parallel or antiparallel to one another.

A first sequence of nucleobases can specifically bind in the major or minor groove of a double-stranded nucleic acid complex. Further, the bases can simultaneously interact specifically with bases on one or both strands of a double-stranded nucleic acid complex, with which the first sequence is bound. Similarly, the bases of each strand of a double-stranded complex can interact specifically with bases on one or both strands of a double-stranded complex in quadruplex aptamers of the invention.

In certain triplex and quadruplex embodiments, each nucleobase binds to one or two other nucleobases. Thus, in addition to the traditional duplex Watson-Crick base pairs and the duplex homologous base pairs described above, such embodiments include the following Watson-Crick base binding triplets: A:T:A, T:A:T, U:A:T, T:A:U, A:U:A, U:A:U, G:C:G and/or C:G:C (including $C^+$:G:C, and/or any other ionized species of base), and/or the following homologous base triplets: A:A:T, T:T:A, U:U:A, T:U:A, A:A:U, U:T:A, G:G:C and/or C:C:G (including C:$C^+$:G, and/or any other ionized species of base).

Thus, in certain quadruplex embodiments wherein the aptamer comprises first, second, third and fourth strands, it is believed that the bases of the first and third strands bind to each other, in addition to: (a) the binding between opposing bases of the first and second strands; (b) the binding between opposing bases of the third and fourth strands; and (c) the binding between opposing bases of the second and fourth strands.

In certain embodiments of the triplex and quadruplex aptamers of the invention, no binding sequence of bases is contiguous with another binding sequence of bases. That is, there are at least three separate strands. Although folded conformations and the like (e.g., hairpin turns, etc.) are within the scope of the invention (particularly when the aptamer is complexed with target molecules, such as proteins), folded portions of a single strand do not make the strand count more than once in our descriptions of the invention.

Aptamers of the invention preferably do not rely on Hoogsteen bonding or G—G quartets for maintenance of the complex structure, although Hoogsteen bonding and/or G—G quartets may be present. That is, aptamers of the invention are preferably substantially free of Hoogsteen bonding, and substantially free of G—G quartets.

Each strand of the aptamer independently comprises a nucleic acid having a deoxyribose phosphate or ribose phosphate backbone (e.g., DNA, RNA, mRNA, hnRNA, rRNA, tRNA or cDNA) or a nucleic acid analogue thereof. Preferred nucleic acid analogues contain an uncharged or partially negatively charged backbone (i.e., a backbone having a charge that is not as negative as a native DNA backbone), and include, e.g., PNA and LNA. Certain embodiments are free of PNA. Nucleic acid analogues of the invention can also comprise partially positively charged backbones.

At least a portion of the aptamer may be isolated, purified, artificial or synthetic.

In embodiments, a portion of the aptamer is a PCR amplified product.

The aptamers of the invention can be present in solution, on a solid support, in vitro, in vivo or in silico. The solid support can be electrically conductive (e.g., an electrode) or non-conductive. In addition, the complexes can be optically mapped or sequenced after being elongated, as taught in U.S. Pat. Nos. 6,147,198 and 5,720,928 to Schwartz.

Aptamers of the invention can be provided by a method comprising: (a) providing a hybridization mixture comprising a first single-stranded or double-stranded moiety containing a first heteropolymeric sequence of nucleic acids or nucleic acid analogues, a second single-stranded or double-stranded moiety containing a second heteropolymeric sequence of nucleic acids or nucleic acid analogues, water, and a buffer; and (b) incubating said hybridization mixture for an incubation time effective to hybridize said first heteropolymeric sequence to said second heteropolymeric sequence to provide the aptamer.

The hybridization mixture can include any conventional medium known to be suitable for preserving nucleotides. See, e.g., Sambrook et al., "Molecular Cloning: A Lab Manual," Vol. 2 (1989). For example, the medium can comprise nucleotides, water, buffers and standard salt concentrations. When divalent cations are used exclusively to promote triplex or quadruplex formation, chelators such as EDTA or EGTA should not be included in the reaction mixtures.

Specific binding between bases occurs under a wide variety of conditions having variations in temperature, salt concentration, electrostatic strength, and buffer composition. Examples of these conditions and methods for applying them are known in the art. Our copending U.S. patent application No. 09/885,731, filed Jun. 20, 2001, discloses conditions particularly suited for use in this invention.

Unlike many Hoogsteen-type complexes, which are unstable or non-existent at pH levels above about 7.6, the complexes of the invention are stable over a wide range of pH levels, preferably from about pH 5 to about pH 9.

Aptamers of the invention can be provided for analytic, diagnostic, prophylactic, therapeutic and/or engineering purposes. The complexes can be used to analyze, diagnose, prevent and/or treat conditions associated with infection by an organism or virus. The organism or virus can be quantitated, if desired.

An aptamer of the invention can be used as a separation tool for retrieving targets to which it specifically binds. In this situation, the aptamer is functioning much like a monoclonal antibody in both its specificity and function. By coupling such an aptamer containing the specifically binding sequence to a solid support, desired target substances can be recovered. This is particularly useful in research or manufacturing in effecting the isolation and purification of substances to which they bind.

In diagnostic applications, the inventive aptamers can be employed in specific binding assays for target substances. They can be labeled using methods and labels known in the art including, but not limited to, detectable moieties such as fluorophores and radioisotopes, and then used for in vivo imaging or histological analysis. Because of their high specificity, one application of the aptamers is detecting differences in the type and level of post-translational protein modifications, and even the presence of mutant proteins.

Therapeutically, the aptamer can specifically bind to biologically active sites on the target molecule and affect biological activity. "Biological activity" is used herein to describe any activity that the target possesses in the normal context of its metabolic or other in vivo function in the organism. Without limiting the invention, this can include the catalytic function of an enzyme, or ribozyme, the regulatory function of a hormone, or the recognition function of a cell surface molecule.

The aptamers can be formulated for a variety of modes of administration, including systemic and topical or localized administration. For systemic administration the aptamer can be given via inhalation or injection, including intramuscular, intravenous, intraperitoneal and subcutaneous. Administration can also be transmucosal or transdermal as well as orally.

The aptamers can also be used in expression systems, for example in applying gene therapy.

In certain embodiments, the aptamer can be a drug or can be formed as an anti-cancer agent, autopathogen agent or to effect cellular regulation or transcription as well as gene expression. The aptamer can stimulate an immune response or apoptosis.

This invention enables aptamer binding in a living organism or virus, or in a cell. The complex can be formed in solution, attached to a surface or substrate, a partition, a bead or an electrode or biochip. The utility of these biochips can be found in, but not limited to, forming molecular fingerprints of tissue samples, analysis of molecular response to viral infection, analysis of inflammation response and analysis of biochemical pathways.

Aptamers of the invention can be formed under conventional hybridization conditions, under triplex hybridization conditions, under quadruplex hybridization conditions or under conditions of in situ hybridization. It is preferred that complexes be formed at a temperature of about 2° C. to about 55° C. for about two hours or less. In certain embodiments, the incubation time is preferably less than five minutes, even at room temperature. Longer reaction times may not be required, but incubation for up to 24 hours in many cases may not adversely affect the complexes. The fast binding times of the complexes of the invention contrast with the much longer binding times necessary for the formation of Hoogsteen bound complexes. Portions of the aptamers may be crosslinked by the many means of crosslinking known in the art. Aptamers may comprise unpaired nucleobases and non-nucleobase molecules.

The promoter in the hybridization medium is preferably an intercalating agent or a cation, as disclosed in U.S. patent application No. 09/613,263, filed Jul. 10, 2000. The intercalators are optionally fluorescent. The intercalating agent can be, e.g., a fluorophore, such as a member selected from the group consisting of YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, cyanine monomers, ethidium bromide, ethidium homodimer-1, ethidium homodimer-2, ethidium derivatives, acridine, acridine orange, acridine derivatives, ethidium-acridine heterodimer, ethidium monoazide, propidium iodide, SYTO dyes, SYBR Green 1, SYBR dyes, Pico Green, SYTOX dyes and 7-aminoactinomycin D.

Suitable cations include, e.g., monovalent cations, such as $Na^+$ (preferably at a concentration of 40 mM to 200 mM), $K^+$ (preferably at a concentration of 40 mM to 200 mM), and other alkali metal ions; divalent cations, such as alkaline earth metal ions (e.g., $Mg^{+2}$ and $Ca^{+2}$) and divalent transition metal ions (e.g., $Mn^{+2}$, $Ni^{+2}$, $Cd^{+2}$, $Co^{+2}$ and $Zn^{+2}$); and cations having a positive charge of at least three, such as $Co(NH_3)_6^{+3}$, trivalent spermidine and tetravalent spermine. $Mn^{+2}$ is preferably provided at a concentration of 10 mM to 45 mM. $Mg^{+2}$ is preferably provided at a concentration of 10 mM to 45 mM. $Ni^{+2}$ is preferably provided at a concentration of about 20 mM. In embodiments, $Mg^{+2}$ and $Mn^{+2}$ are provided in combination at a concentration of 1 mM each, 2 mM each, 3 mM each . . . 40 mM each (i.e., 1–40 mM each).

The amount of cation added to the medium in which the complex forms depends on a number of factors, including the nature of the binding to occur, the nature of the cation, the concentration of binding strands, the presence of additional cations and the base content of the probe and target. The preferred cation concentrations and mixtures can routinely be discovered experimentally. For triplexes, it is preferred to add cation(s) to the medium in the following amounts: (a) 10 mM–30 mM $Mn^{+2}$; (b) 10 mM–20 mM $Mg^{+2}$; (c) 20 mM $Ni^{+2}$; or (d) 1 mM–30 mM of each of $Mn^{+2}$ and $Mg^{+2}$. For quadruplexes, it is preferred to add cation(s) to the medium in the following amounts: (a) 10 mM–45 mM $Mn^{+2}$; (b) 10 mM–45 mM $Mg^{+2}$; or (c) 10 mM–40 mM of each of $Mn^{+2}$ and $Mg^{+2}$.

Although not required, other binding promoters include, e.g., single stranded binding proteins such as Rec A protein, T4 gene 32 protein, *E. coli* single stranded binding protein, major or minor nucleic acid groove binding proteins, viologen and additional intercalating substances such as actinomycin D, psoralen, and angelicin. Such facilitating reagents may prove useful in extreme operating conditions, for example, under abnormal pH levels or extremely high temperatures. Certain methods for providing complexes of the invention are conducted in the absence of protein promoters, such as Rec A and/or other recombination proteins.

In addition to providing novel aptamers, the invention also provides a rapid, sensitive, environmentally friendly, and safe method for assaying binding between aptamers and targets.

Embodiments of the invention comprise calibrating the measured signal (e.g., optical, fluorescence, chemiluminescence, electrochemiluminescence, electrical or electromechanical properties) for a first aptamer-target mixture against the same type of signal exhibited by other aptamers combined with the same target, wherein each of the other aptamers differs from the first aptamer by at least one nucleobase.

A calibration curve can be generated, wherein the magnitude of the measured signal (e.g., fluorescent intensity) is a function of the binding affinity between the target and aptamer.

In embodiments, the signal measured can be the fluorescent intensity of a fluorophore included in the test sample. In such embodiments, the binding affinity between the aptamer and target can be directly or inversely correlated with the intensity, depending on whether the fluorophore signals hybridization through signal quenching or signal amplification. Under selected conditions, the fluorescent intensity generated by intercalating agents can be directly correlated with aptamer-target binding affinity, whereas the intensity of preferred embodiments employing a non-intercalating fluorophore covalently bound to the aptamer or target can be inversely correlated with aptamer-target binding affinity.

The invention enables quantifying the binding affinity between aptamer and target. Such information can be valuable for a variety of uses, including designing drugs with optimized binding characteristics.

The assay of the invention is preferably homogeneous. The assay can be conducted without separating free aptamer and free target from the aptamer-target complex prior to detecting the magnitude of the measured signal. The assay does not require a gel separation step, thereby allowing a great increase in testing throughput. Quantitative analyses are simple and accurate. Consequently the binding assay saves a lot of time and expense, and can be easily automated. Furthermore, it enables binding variables such as buffer, pH, ionic concentration, temperature, incubation time, relative concentrations of aptamer and target sequences, intercalator concentration, length of target sequences, length of aptamer sequences, and possible cofactor (i.e., promoter) requirements to be rapidly determined.

The assay can be conducted in, e.g., a solution within a well or microchannel, on an impermeable surface or on a biochip. In certain embodiments, the target is provided in the hybridization medium before the aptamer, and the aptamer is provided in dehydrated form prior to rehydration by contact with the hybridization medium.

In certain embodiments, the inventive assay is conducted without providing a signal quenching agent on the target or on the aptamer.

Aptamers of the invention are preferably 2 to 100 bases long (more preferably 5 to 45 bases long), and comprise at least one nucleobase-containing strand. As used herein, the term "nucleobase-containing strand(s)" denotes, e.g., ssDNA, RNA, ssPNA, LNA, dsDNA, dsRNA, DNA:RNA hybrids, dsPNA, PNA:DNA hybrids and other single and double-stranded nucleic acids and nucleic acid analogues having uncharged, partially negatively charged, sugar phosphate and/or peptide backbones. It also denotes nucleobase strands having positively charged or partially positively charged backbones.

The assay of the invention does not require the use of radioactive probes, which are hazardous, tedious and time-consuming to use, and need to be constantly regenerated. Aptamers of the invention are preferably safe to use and stable for years.

Targets of the invention are moieties that are substantially free of nucleobases. Preferred targets include, e.g., proteins, peptides (e.g., peptides, dipeptides, tripeptides, etc.), polypeptides, proteins, multi-protein complexes, hormones, lipids, etc.

A variety of aptamer-target complexes can be assayed with the method of the invention. The invention can be used to analyze binding characteristics (including the presence or absence of binding, and the binding affinity) between an aptamer and, e.g., a peptide, a protein, or a multi-protein complex. Suitable proteins for analysis include, e.g., wild-type, mutant, isolated, in vitro translated, and/or synthesized. The invention is particularly suitable for analyzing binding of DNA-binding protein. Test samples need not be 100% pure, but rather, can comprise, e.g., a purified preparation, a synthesized preparation, a semi-purified protein extract, a crude protein extract, or an in vitro translated preparation.

The aptamer-target complex is preferably detected by a change in at least one label. The at least one label can be attached to the aptamer and/or the target, and/or can be free in the test medium. The at least one label can comprise at least two moieties.

The label is preferably at least one member selected from the group consisting of a spin label, a fluorophore, a chromophore, a chemiluminescent agent, an electrochemiluminescent agent, a radioisotope, an enzyme, a hapten, an antibody and a labeled antibody. Preferably, the complex is detected by at least one emission from the label or by monitoring an electronic characteristic of the complex.

The aptamer-target complex can be detected under at least one varied condition, such as disclosed in U.S. Pat. No. 6,265,170 to Picard et al. Suitable varied conditions include, e.g., (a) a change in nonaqueous components of the test medium, (b) a change in a pH of the test medium, (c) a change in a salt concentration of the test medium, (d) a change of an organic solvent content of the test medium, (e) a change in a formamide content of the test medium, (f) a change in a temperature of the test medium, and (g) a change in chaotropic salt concentration in the test medium. In addition, the varied condition can be the application of a stimulus, such as, e.g., electric current (DC and/or AC), photon radiation (e.g., laser light), or electromagnetic force. The stimulus can be applied constantly or pulsed. Detection can be accomplished through the use of a single varied condition, or through a combination of conditions varied serially.

The response of a characteristic of the aptamer-target complex in the test medium to the varied condition or stimulus can be monitored to detect the complex. The characteristic can be, e.g., electrical conductance or Q (a resonant structure of a transmission line or changes in phase or amplitude of a signal propagated in the transmission line in the test medium).

In embodiments, the detection method comprises: (a) detecting a signal from a label, wherein the signal is correlated to a binding affinity between the aptamer and the target; (b) varying a condition of a test medium; (c) detecting a subsequent signal; and (d) comparing the signal and the subsequent signal. The varying and the detecting can be repeated at least once or performed only once.

The label is preferably a fluorophore. Both intercalating and non-intercalating fluorophores are suitable for use in the invention. The fluorophore can be free in solution, covalently bound to the aptamer and/or covalently bound to the target. When the fluorophore is covalently bound to the aptamer, it is preferably bound to an end thereof. Preferred fluorescent markers include biotin, rhodamine, acridine and fluorescein, and other markers that fluoresce when irradiated with exciting energy. Suitable non-intercalating fluorophores include, e.g., alexa dyes, BODIPY dyes, biotin conjugates, thiol reactive probes, fluorescein and its derivatives (including the "caged probes"), Oregon Green, Rhodamine Green and QSY dyes (which quench the fluorescence of visible light excited fluorophores).

The excitation wavelength is selected (by routine experimentation and/or conventional knowledge) to correspond to this excitation maximum for the fluorophore being used, and is preferably 200 to 1000 nm. Fluorophores are preferably selected to have an emission wavelength of 200 to 1000 nm. In preferred embodiments, an argon ion laser is used to irradiate the fluorophore with light having a wavelength in a range of 400 to 540 nm, and fluorescent emission is detected in a range of 500 to 750 nm.

The assay of the invention can be performed over a wide variety of temperatures, such as, e.g., from about 2 to about 60° C. Certain prior art assays require elevated temperatures, adding cost and delay to the assay. On the other hand, the invention can be conducted at room temperature or below (e.g., at a temperature below 25° C.).

The invention will be illustrated in more detail with reference to the following Examples, but it should be understood that the present invention is not deemed to be limited thereto.

EXAMPLES

The Examples demonstrate the binding of three different classes of DNA-binding proteins to their respective DNA recognition sites, and the detection of the complex formed. The three representative proteins selected for the Examples are c-JUN (Examples 1, 2 and 4), Sp1 (Example 3) and Oct-1 (Examples 5–6).

Example 1 c-JUN is a member of the AP-1 family of transcription factors that bind and regulate AP-1 DNA-binding sites naturally present in promoter or enhancer sequences of many cellular and viral genes. See, e.g., Bohmann et al., "Human proto-oncogene c-jun encodes a DNA binding protein with structural and functional properties of transcription factor AP-1." 238 Science 1386–1392 (1987). Furthermore, the human c-JUN protein belongs to a class of proteins (that include c-FOS and c-MYC), designated proto-oncoproteins, which when deregulated and activated, cause tumorigenesis and cancer. c-JUN, c-FOS and c-MYC constitute a specific group of DNA-binding proteins, whose DNA-binding domain consists of a region rich in basic amino acids (commonly called the "basic region" or "basic domain") that lies immediately adjacent to a structural domain, designated the "leucine zipper". The leucine zipper consists of 4 to 5 leucine residues (c-JUN has 5), that are separated at regular intervals of 7 amino acids, which form bimolecular coiled-coiled structures. Specific contact with its palindromic DNA sequence occurs primarily via the basic region. The leucine zipper allows dimerization of c-JUN to itself, forming c-JUN:c-JUN homodimers, or to c-FOS forming c-JUN:c-FOS heterodimers. Homodimers of c-JUN bend duplex DNA 79° inward in the minor groove of a DNA helix, while c-JUN:c-FOS heterodimers bend duplex DNA 94° in the opposite orientation, inward in the major groove. A fully functional DNA-binding domain requires both the basic region and the leucine zipper. As pure human c-JUN protein is used in the following assays, the examples show binding of c-JUN:c-JUN homodimers to a single AP-1 site (JD1F/2F).

A fluorescein labeled wild-type dsDNA oligonucleotide, JD1F/2F, containing a consensus 7 bp AP-1 DNA binding site, was derived from the promoter sequence of the human collagenase gene. Complementary 5'-fluorescein labeled ssDNA 17-mers JD1F and JD2F, having 5 nucleotides flanking both ends of the consensus AP-1 site, were synthesized on a PerSeptive Biosystems Expedite nucleic acid synthesizer and purified by HPLC. Equimolar amounts of JD1F and JD2F oligos were annealed in 10 mM Tris, pH 7.5, 100 mM NaCl, 1 mM EDTA by denaturation at 95° C. for 5 minutes, followed by incubation at 42° C., 35° C. and 21° C. for 40 minutes each. Annealed oligos were ethanol precipitated for 2 hours at −20° C., pelleted by centrifugation at 14K rpm for 20 minutes at 0° C., washed with 100% ethanol, repelleted at 14K rpm for 20 minutes at 0° C., dried and dissolved in ddH$_2$O at a final concentration of 100 ng/μl. The dsDNA oligos formed had a single fluorescein molecule on both 5' ends.

```
Sequence for wild-type JD1F (SEQ ID NO:1):
5'-Flu-GTG TCT GAC TCA TGC TT-3'

Sequence for wild-type JD2F (SEQ ID NO:2):
5'-Flu-AAG CAT GAG TCA GAC AC-3'
```

Mutant dsDNA 17-mer JD3F/4F was identical in sequence to wild-type JD1F/2F, except for a single base pair change (underlined) from GC to TA within the wild-type AP-1 consensus DNA-binding site.

```
Sequence for mutant JD3F (SEQ ID NO:3):
5'-Flu-GTG TCT TAC TCA TGC TT-3'

Sequence for mutant JD4F (SEQ ID NO:4):
5'-Flu-AAG CAT GAG TAA GAC AC-3'
```

The c-JUN:DNA binding reaction mixture (30 μl) contained the following: 9.25 mM HEPES, pH 7.9, 2.23 mM MgCl$_2$, 0.03 mM EDTA, 50 mM NaCl, 5.0 mM DTT, 3.75% (v/v) glycerol, 0.15 μg/μl bovine serum albumin (BSA), 0–2.0 μg pure c-JUN protein (Promega, Madison, Wis.) or 0–400 ng pure c-JUN peptide, and 0.075 pmole 5'-fluorescein labeled dsDNA oligonucleotide. When full-length c-JUN was used, 3 ng/μl poly(dI)—poly(dC) was included in the reaction mix, and added before the addition of protein and fluorescein-labeled DNA. The examples in FIGS. 1B and 1D contained 50 mM KCl in lieu of 50 mM NaCl. Wild-type and mutant c-JUN DNA-binding domain peptides were generously supplied by Dr. Dirk Bohmann (European Molecular Biology Laboratory, Heidelberg, Germany). The reaction mixtures were incubated at 21° C. for 30 minutes, placed into a quartz cuvette, irradiated with an argon ion laser beam having a wavelength of 488 nm and monitored for fluorescent emission.

The wild-type c-JUN DNA-binding domain peptide consisted of the C-terminal 132 amino acid residues of c-JUN (from Gln 209 to Phe 340). The c-JUN mutant 14 DNA-binding domain peptide was identical in sequence to the wild-type peptide, except for a two amino acid substitution (underlined) that converted lysine to isoleucine at position 277 and cysteine to aspartic acid at position 278, within the central basic domain.

```
Sequence for wild-type c-JUN peptide (SEQ ID NO:5):
     210              220              230              240
 Q P Q Q Q Q Q P P H H L P Q Q M P V Q H P R L Q A L K E E P Q T V P E M P G E 250              260              270              280
 T P P L S P I D M E S Q E R I K A E R K R M R N R I A A S K C R K R K L E R I A 290              300              310              320
 R L E E K V K T L K A Q N S E L A S T A N M L R E Q V A Q L K Q K V M N H V 330              340
 N S G C Q L M L T Q Q L Q T F Sequence for mutant 14 c-JUN peptide (SEQ ID NO:6):
     210              220              230              240
 Q P Q Q Q Q Q P P H H L P Q Q M P V Q H P R L Q A L K E E P Q T V P E M P G E
```

-continued

```
        250               260               270               280
T P P L S P I D M E S Q E R I K A E R K R M R N R I A A S I D R K R K L E R I A 290               300               310               320
R L E E K V K T L K A Q N S E L A S T A N M L R E Q V A Q L K Q K V M N H V 330               340
N S G C Q L M L T Q Q L Q T F
```

Figure 1B:
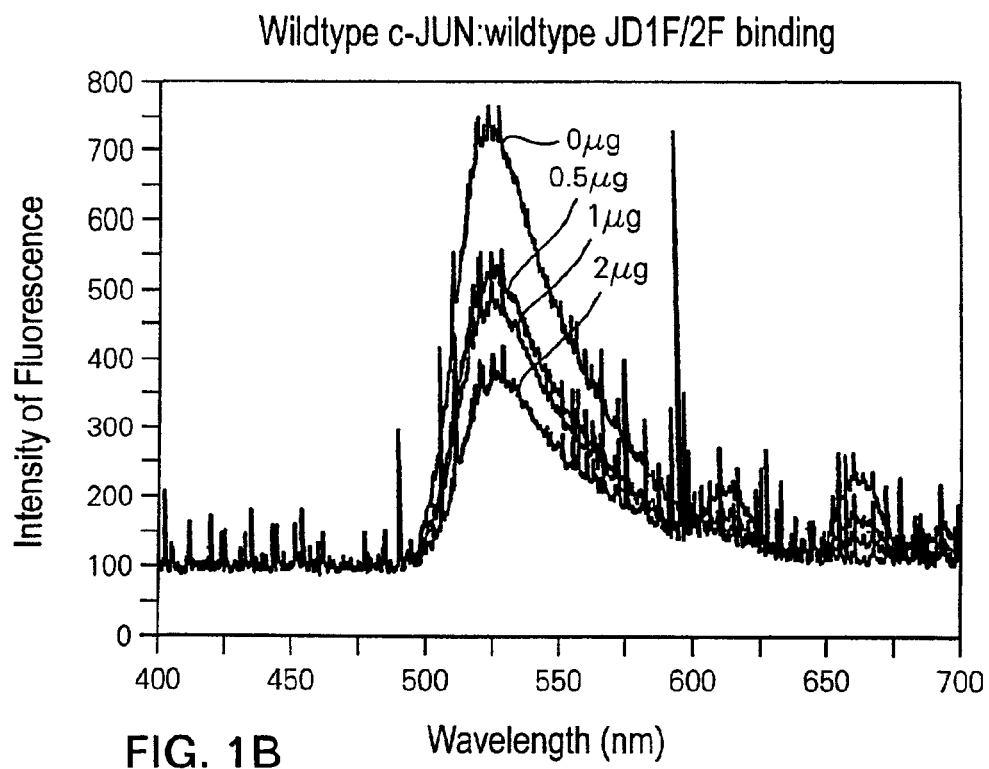
Figure 1C:
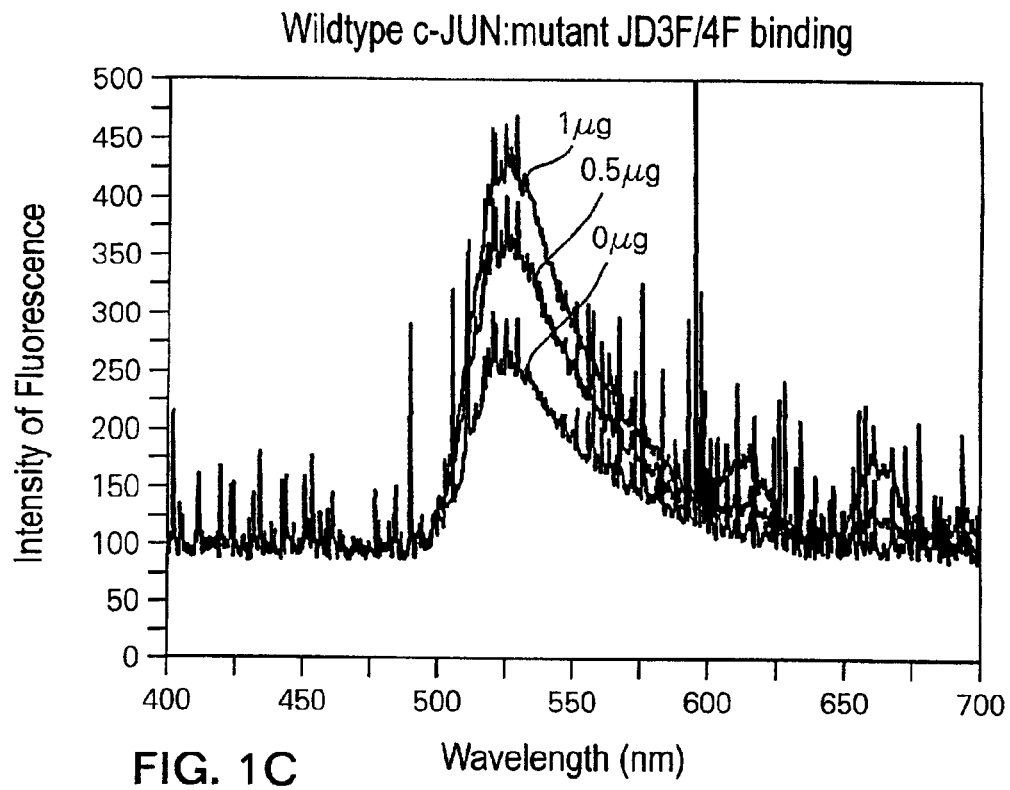
Figure 1D:
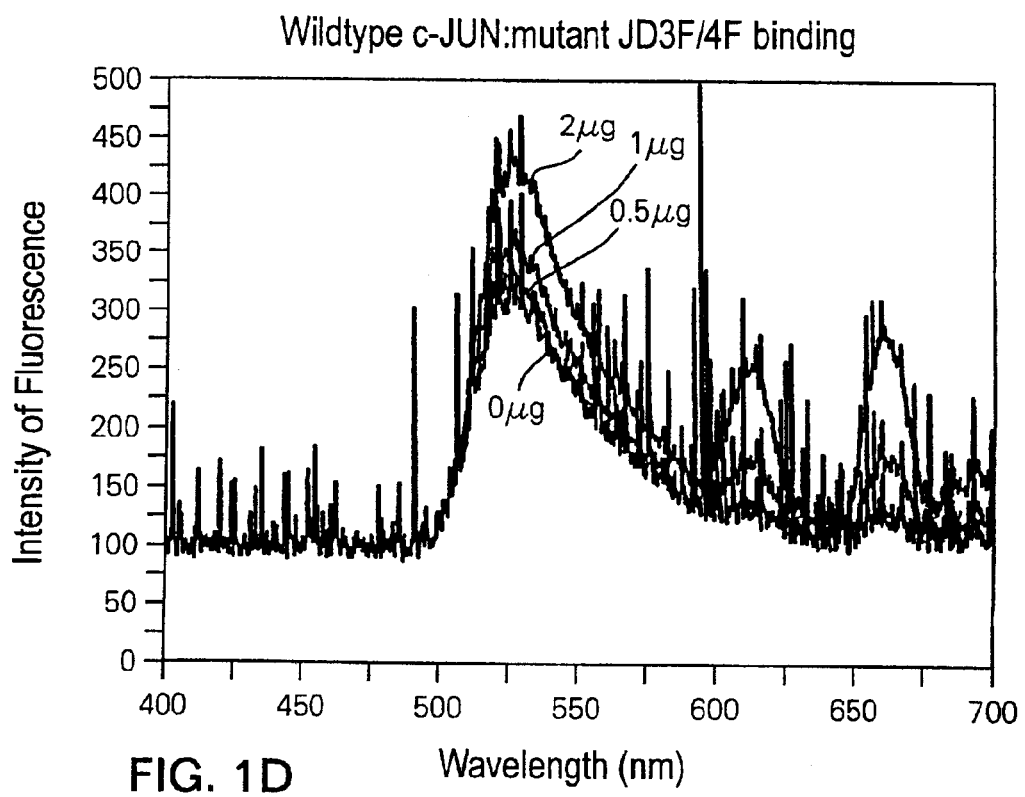

The fluorescence spectra obtained for the binding of 2 µg, 1 µg or 0.05 µg full length c-JUN to 0.075 pmole wild-type JD1F/2F or 0.075 pmole mutant JD3F/4F are shown in FIGS. 1A–1D. The DNA concentration was kept constant at 2.5 fmole/µl for every sample tested. All samples, whether DNA alone, or in the presence of c-JUN, were tested under identical reaction conditions. The maximum fluorescent intensity occurred at 525 nm, since the fluorophore used was fluorescein. The maximum intensity observed when 1 µg or 0.05 µg c-JUN was bound to JD1F/2F was 54% and 49% lower, respectively, than that observed with JD1F/2F alone (FIG. 1A). A 55% decrease in intensity resulted when 2 µg c-JUN was bound to wild-type JD1F/2F (data not shown). The similar decreases in intensity obtained with both 1 µg and 2 µg c-JUN, suggest that saturation levels of binding were achieved by addition of 1 µg protein.

To test c-JUN's preference for binding duplex DNA under different salt conditions, the above experiment was performed simultaneously in a reaction buffer containing 50 mM KCl instead of 50 mM NaCl (FIG. 1B). When 2 µg c-JUN was bound to wild-type JD1F/2F in the KCl reaction buffer, a 57% decrease in intensity was observed, compared to the level achieved with DNA alone. 1 µg and 0.5 µg c-JUN bound to wild-type JD1F/2F in the 50 mM KCl buffer, yielded a 40% and 34% decrease, respectively, suggesting below saturation levels of binding. Therefore, c-JUN binds to its AP-1 site with higher binding affinity in a 50 mM NaCl reaction mix than in a 50 mM KCl reaction mix. Thus, the laser binding assay according to the invention could not only reliably detect c-JUN:DNA binding, but could also identify preferential binding conditions.

During the same experiment, when the exact same amounts of c-JUN were reacted with 0.075 pmole mutant JD3F/4F in the 50 mM NaCl reaction mix (FIG. 1C) or the 50 mM KCl reaction mix (FIG. 1D), no decrease in fluorescent intensity was observed in every sample, indicating non-binding of protein to the mutated DNA sequence. These mutant DNA binding studies confirm the specificity of both the c-JUN:wild-type DNA binding conditions and the laser detection method.

Identical results were obtained when the emitted fluorescent intensities were measured at three different integration times (data not shown), demonstrating consistent results irrespective of the integration time.

Example 2

Full-length c-JUN protein is 40 KDa or 340 amino acids in size. The DNA-binding domain of c-JUN is localized to the C-terminal 132 amino acid residues of c-JUN (from glutamine at residue 209 to phenylalanine at residue 340), and is able to bind duplex DNA with similar binding affinity as the full-length protein.

Figure 2A:
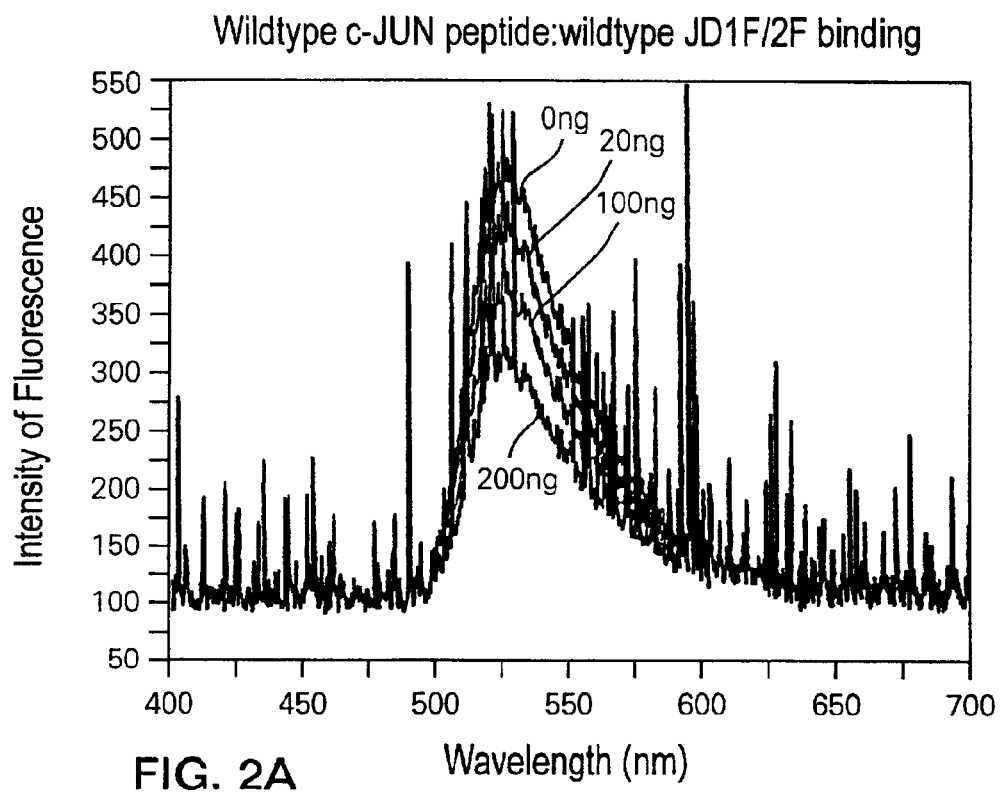
Figure 2B:
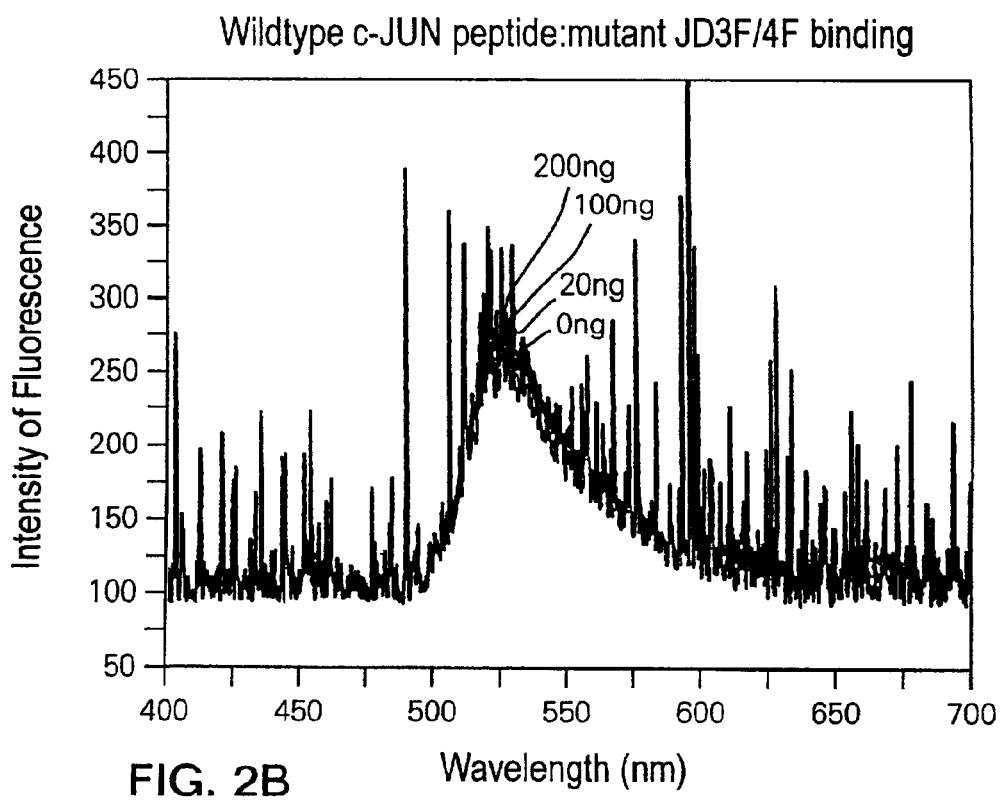

FIGS. 2A–2B demonstrate that binding and detection of duplex DNA binding to such a peptide, consisting of only this 132 amino acid DNA-binding domain. 20 ng, 100 ng and 200 ng of wild-type c-JUN DNA-binding domain peptide bound to 0.075 pmole wild-type JD1F/2F in the 50 mM NaCl reaction mix, resulted in a 13%, 28% and 43% decrease in fluorescent intensity, respectively, compared to the intensity emitted by JD1F/2F alone (FIG. 2A). The fact that the binding of just 20 ng of c-JUN peptide to 0.075 pmole DNA could be reliably detected, demonstrates the high sensitivity of the laser assay. Moreover, the peptide:DNA binding assay is quantitative since increasing amounts of c-JUN peptide resulted in progressively more binding to wild-type DNA.

By contrast, 20 ng, 100 ng and 200 ng wild-type c-JUN peptide did not bind mutant JD3F/4F, resulting in minor increases in fluorescent intensity above that observed with mutant DNA alone (FIG. 2B), confirming the specificity of the laser binding assay.

The 43% decrease in fluorescent intensity observed for 200 ng of c-JUN peptide bound to JD1F/2F, is less than the 54% and 49% decreases observed for 1 µg and 0.5 µg full length c-JUN protein, respectively, as predicted. One would expect to get less static quenching occurring with a peptide, than with a full length protein, since less mass of protein would absorb the emitted fluorescent light in a peptide.

Example 3

Sp1 belongs to a significant class of duplex DNA-binding proteins designated zinc finger DNA-binding proteins. See, e.g., Kadonaga et al., "Isolation of cDNA encoding transcription factor Sp1 and functional analysis of the DNA binding domain." 51 Cell 1079–1090 (1987). Sp1 controls the transcription of a large number of viral and cellular promoters or enhancers, including the HIV-I long terminal repeat (LTR). The number, spacing, orientation and sequence of Sp1 binding sites vary widely between promoters, resulting in high, medium or low affinity binding sites. Although Sp1 is a relatively large protein (95 KDa and 105 KDa in its glycosylated and phosphorylated form), its DNA-binding activity is localized near the C-terminus of the protein (from cysteine at residue 539 to histidine at residue 619). This region contains three contiguous Zn(II) finger motifs, which are metalloprotein structures that interact with DNA. Sequence specificity of DNA binding is conferred entirely by the three Zn(II) fingers. Finger 3 is the most critical finger (with respect to binding affinity), followed by finger 2 and lastly finger 1. Two cysteine and two histidine residues bind a Zn(II) ion to form each finger. Removal of zinc collapses the secondary structure of the three zinc fingers. The fingers in this class of duplex DNA-binding proteins have a consensus sequence of $Cys-X_{2,4}-Cys-X_3-Phe-X_5-Leu-X_2-His-X_3-His$, referred to as $Cys_2/His_2$ fingers. A second type of Zn(II) finger motif, referred to as $Cys_2/Cys_2$ fingers with the form of $Cys-X_2-Cys-X_{13}-Cys-X_2-Cys$, are found in other DNA-binding proteins, such as many hormone receptors.

A wild-type fluorescein labeled dsDNA oligonucleotide, JD11F/12F, containing a single consensus 10 bp Sp1 DNA binding site, was derived from the promoter sequence of the human metallothionein-II$_A$ gene. Complementary 5'-fluorescein labeled ssDNA 20-mers JD11F and JD12F were synthesized, purified and annealed as above.

```
Sequence for wild-type JD11F (SEQ ID NO:7):
5'-Flu-CCG GCC GGG GCG GGG CTT TT-3'

Sequence for wild-type JD12F (SEQ ID NO:8):
5'-Flu-AAA AGC CCC GCC CCG GCC GG-3'
```

Mutant dsDNA 20-mer JD13F/14F was identical in sequence to wild-type JD11F/12F, except for a 6 bp change (underlined) which converted the consensus Sp1 binding site GGG GCG GGG C to TAA ATA GGG C.

```
Sequence for mutant JD13F (SEQ ID NO:9):
5'-Flu-CCG GCC TAA ATA GGG CTT TT-3'

Sequence for mutant JD14F (SEQ ID NO:10):
5'-Flu-AAA AGC CCT ATT TAG GCC GG-3'
```

The Sp1:DNA binding reaction mixture (30 μl) contained the following: 25 mM HEPES, pH 7.8, 100 mM KCl, 100 μM ZnSO$_4$, 1 mM DTT, 20% (v/v) glycerol, 0.05 μg/μl BSA, 0–200 ng pure Sp1 protein (Promega) and 0.1 pmole 5'-fluorescein labeled dsDNA oligonucleotide. The reaction mixes were incubated at 0° C. for 15 minutes, placed into a quartz cuvette, irradiated with an argon ion laser beam having a wavelength of 488 nm and monitored for fluorescent emission.

Figure 3A:
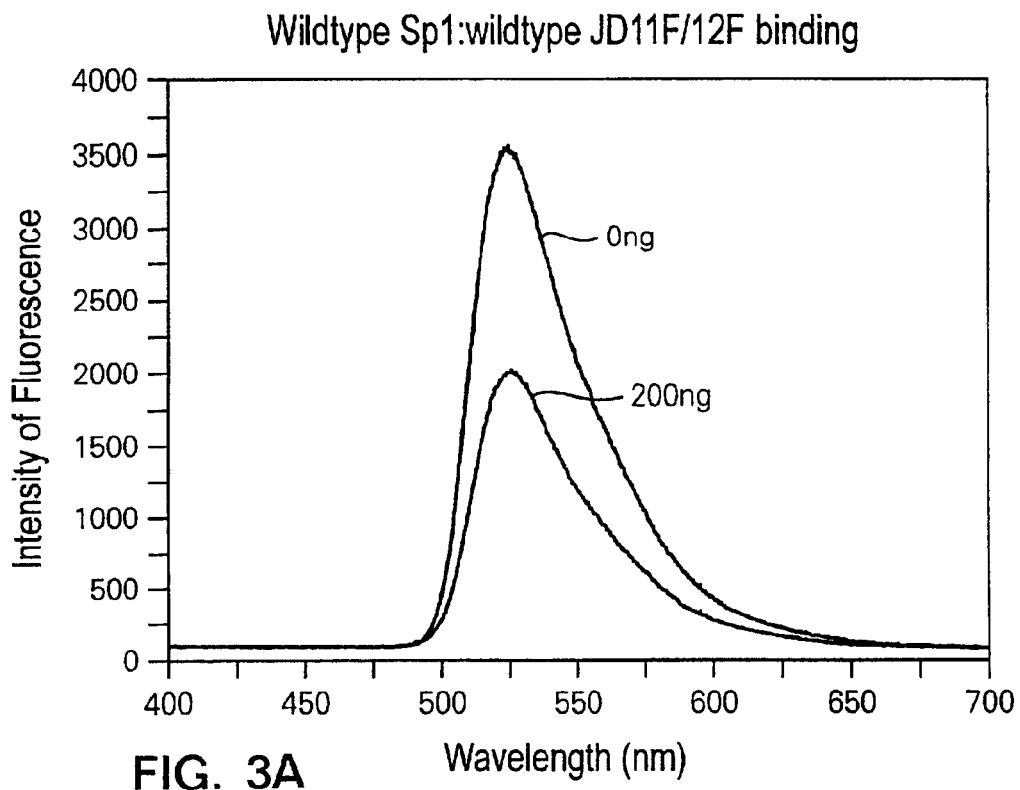

FIG. 3 illustrates the binding of the zinc finger DNA-binding protein Sp1 to wild-type JD11F/12F or mutant JD13F/14F. When 200 ng Sp1 was bound to 0.1 pmole JD11F/12F, a 44% decrease in fluorescent intensity was observed, compared to the intensity level achieved with JD11F/12F alone (FIG. 3A). Furthermore, the binding of 25 ng of full length Sp1 protein could be reliably detected (data not shown), demonstrating the high sensitivity of the laser assay. Since Sp1 is a relatively large protein (95 KDa), while c-JUN is only 40 KDa in size, a lesser amount of protein was required to achieve a 44% reduction in fluorescent intensity for Sp1-bound DNA than c-JUN-bound DNA, due to greater absorption and retention of emitted fluorescent light by the larger protein.

When 200 ng Sp1 was reacted with 0.1 pmole mutant JD13F/14F, no decrease in fluorescent intensity was observed (FIG. 3B), indicating non-binding of protein to the mutated DNA sequence. These studies confirmed the specificity of the laser detection assay for a completely different class of DNA-binding proteins.

Example 4

This example illustrates the ability of the method of the invention to study the binding of an antibody directed to a specific protein, which is directly bound to the labeled DNA sequence. Addition of specific antibodies to protein:DNA complexes (especially multi-protein:DNA complexes) is a technique used to identify the presence of unknown proteins in protein:DNA complexes. The binding of the antibody will either inhibit or totally prevent the protein:DNA complex from forming (resulting in a minimal decrease or no change in fluorescent intensity when compared to free DNA) or will result in an antibody:protein:DNA complex that decreases the intensity of fluorescence even more than the protein:DNA complex.

1 μg, 500 ng and 250 ng c-JUN were reacted with 0.075 pmole of wild-type JD1F/2F in the 50 mM NaCl or 50 mM KCl reaction mix as previously described. After a 15 minute incubation at 21° C., variable amounts of the monoclonal IgG$_1$ antibody, c-JUN (KM-1) (from Santa Cruz Biotechnology, Santa Cruz, Calif.), raised against a peptide corresponding to amino acids 56 to 69 of human c-JUN, was added to some of the c-JUN:DNA mixtures. The reaction mixtures were incubated for an additional 40 minutes at 21° C., placed into a quartz cuvette, irradiated with an argon ion laser beam having a wavelength of 488 nm and monitored for fluorescent emission.

Figure 4A:
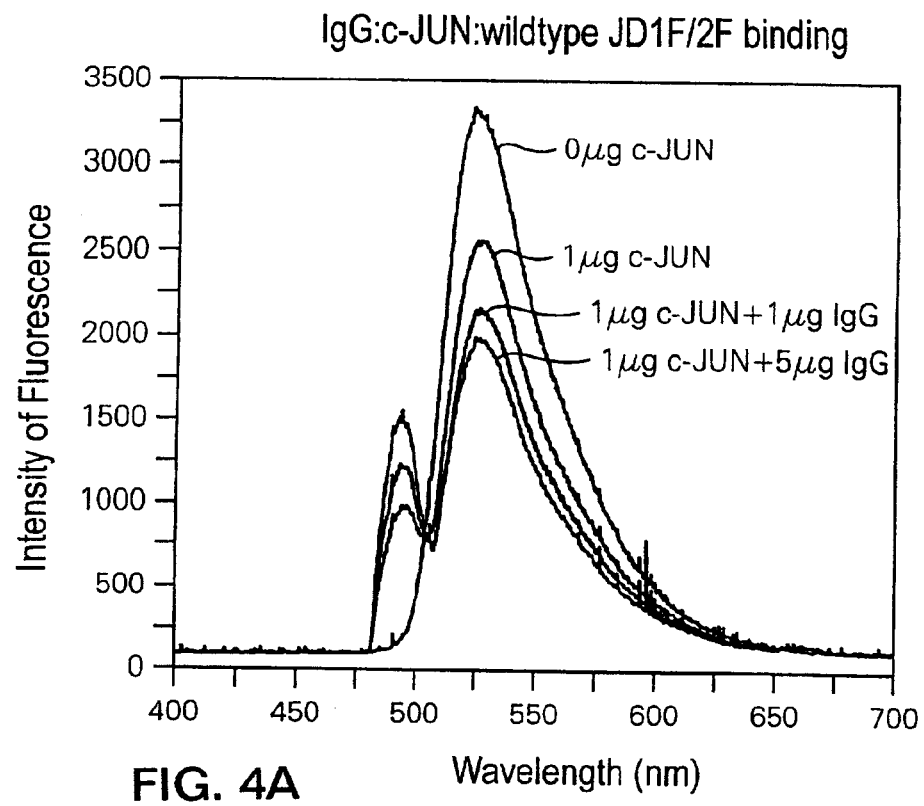
Figure 4B:
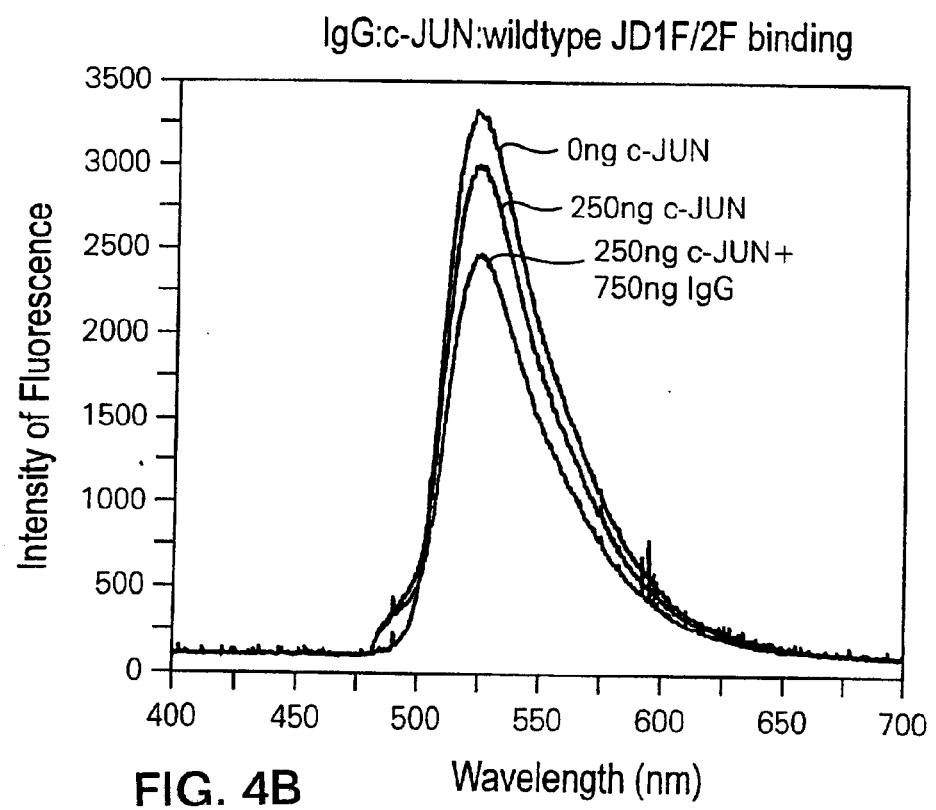

FIGS. 4A and 4B show the binding of 1 μg or 250 ng c-JUN to JD1F/2F, respectively, in the 50 mM NaCl reaction mix. When 1 μg or 250 ng c-JUN was bound to JD1F/2F, a 25% and 11% decrease in intensity, respectively, was observed, compared to the level achieved with DNA alone. Addition of 5 μg or 1 μg of c-JUN antibody to 1 μg c-JUN resulted in a 42% and 37% decrease, respectively (i.e., a further decrease of 17% and 12%), indicative of IgG:c-JUN:DNA complex formation (FIG. 4A). Identical decreases in intensity were observed when c-JUN antibody was bound to 1 μg c-JUN bound to JD1F/2F in the 50 mM KCl reaction mix (data not shown). Similarly, addition of 750 ng of c-JUN antibody to 250 ng c-JUN bound to JD1F/2F, yielded 27% decrease in intensity, a further decrease of 16% from the level achieved from the protein:DNA complex alone (FIG. 4B). IgG:c-JUN complexes did not bind to mutant DNA JD3F/4F (data not shown), confirming the specificity of the laser assay.

This example demonstrates that the laser detection method can differentiate between an antibody:protein:DNA complex and a protein:DNA complex. Moreover, it establishes the ability of the invention to reliably detect heterologous multi-protein complexes bound to DNA and not just monomers or homodimers of protein bound to DNA. Only one of the proteins in the multi-protein:DNA complex needs to be bound to DNA. Multi-protein:DNA complexes, where more than one protein interacts with DNA can also be assayed by the method of the invention.

Example 5

The ubiquitous cellular octamer-binding protein (Oct-1) binds DNA directly by a characteristic DNA-binding domain, which is completely different than the DNA-binding domains of c-JUN or Sp1. Oct-1 is a member of the POU domain DNA-binding proteins, which regulate cell-specific transcription and development. See, e.g., Sturm et al., "The ubiquitous octamer-binding protein Oct-1 contains a POU domain with a homeo box subdomain." 2 Genes and Development 1582–1599 (1988). The structure of the POU domain is unique among DNA-binding domains, because it contains two structurally independent domains that cooperate functionally as a single DNA-binding unit. Oct-1 binds to DNA via this POU domain, composed of a 75 amino acid POU-specific (POUs) domain, a short linker region of 24 amino acids, and a 60 amino acid POU-type homeo (POU$_H$) domain. Both the POU$_S$ domain and the POU$_H$ domain contain helix-turn-helix (HTH) structures.

Unlike Examples 1–4, which used purified protein, this example uses HeLa cell nuclear extracts (from Promega, Madison, Wis.) as the source for Oct-1. The use of HeLa cell nuclear extracts, which contain a vast multitude of various DNA-binding proteins and transcription factors, shows the feasibility of using crude protein extracts to detect sequence-specific protein:DNA binding by the laser assay of the invention.

A wild-type fluorescein labeled dsDNA oligonucleotide, JD49F/50F, containing a single consensus 8 bp Oct-1 DNA binding site, was derived from the human immunoglobulin heavy chain promoter. Complementary 5'-fluorescein labeled ssDNA 18-mers JD49F and JD50F were synthesized, purified and annealed as above.

```
Sequence for wild-type JD49F (SEQ ID NO:11):
5'-Flu-GAG TAT GCA AAT CAT GTG-3'

Sequence for wild-type JD50F (SEQ ID NO:12):
5'-Flu-CAC ATG ATT TGC ATA CTC-3'
```

Mutant dsDNA 18-mer JD51F/52F was identical in sequence to wild-type JD49F/50F, except for a double point mutation ($A_1T_2$ CG) (underlined) that inactivated the $POU_S$ binding site, and a second double point mutation ($A_6A_7$ CC) (underlined) that inactivated the $POU_H$ binding site, thereby converting the consensus Oct-1 binding site ATGCAAAT to CGGCACCT.

```
Sequence for mutant JD51F (SEQ ID NO:13):
5'-Flu-GAG TCG GCA CCT CAT GTG-3'

Sequence for mutant JD52F (SEQ ID NO:14):
5'-Flu-CAC ATG AGG TGC CGA CTC-3'
```

The Oct-1:DNA binding reaction mixture (30 μl) contained the following: 9.25 mM HEPES, pH 7.9, 2.23 mM $MgCl_2$, 0.03 mM EDTA, 63 mM NaCl, 1.0 mM DTT, 3.75% (v/v) glycerol, 0.10 mg/ml BSA, 0.01 mM PMSF, 67 μg/ml poly(dI)-poly(dC), 67 μg/ml poly(dG-dC)-poly(dG-dC), 0–15 μg HeLa cell nuclear extract (Promega) and 0.05 pmole 5'-fluorescein labeled dsDNA oligonucleotide. The relatively high concentrations of poly(dI)-poly(dC) and poly (dG-dC)-poly(dG-dC) are required to ensure sequence specific protein:DNA binding, when using crude nuclear protein extracts. The reaction mixtures were incubated at 21° C. for 30 minutes, placed into a quartz cuvette, irradiated with an argon ion laser beam having a wavelength of 488 nm and monitored for fluorescent emission.

Figure 5A:
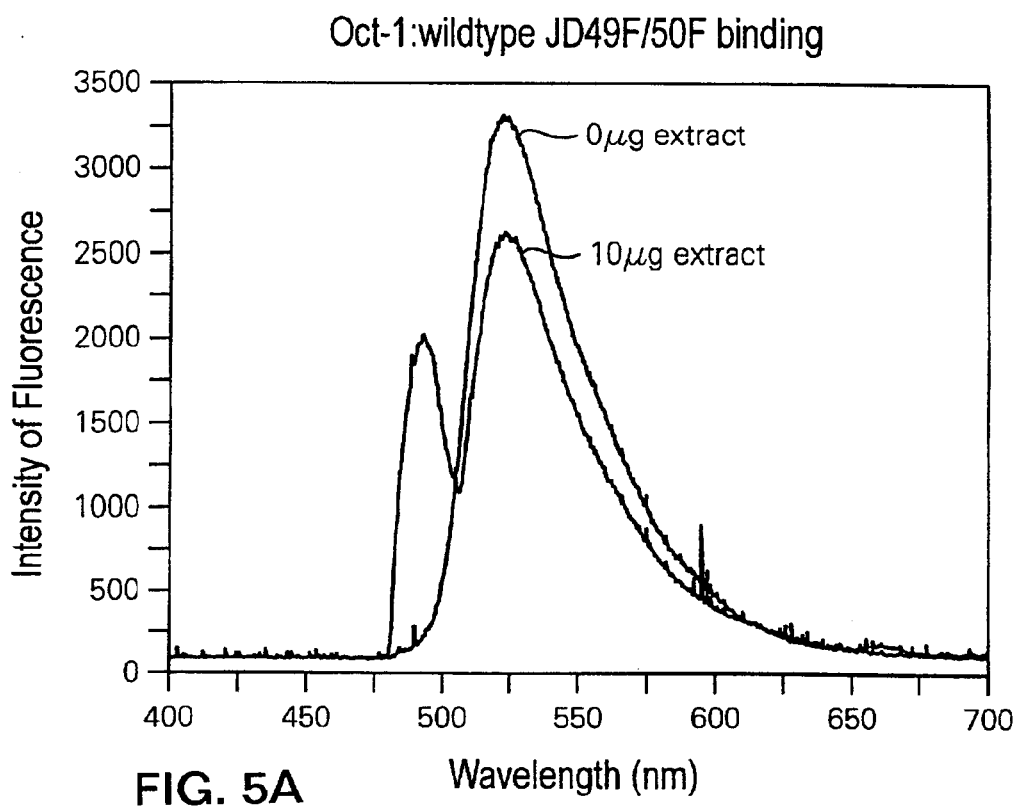
Figure 5B:
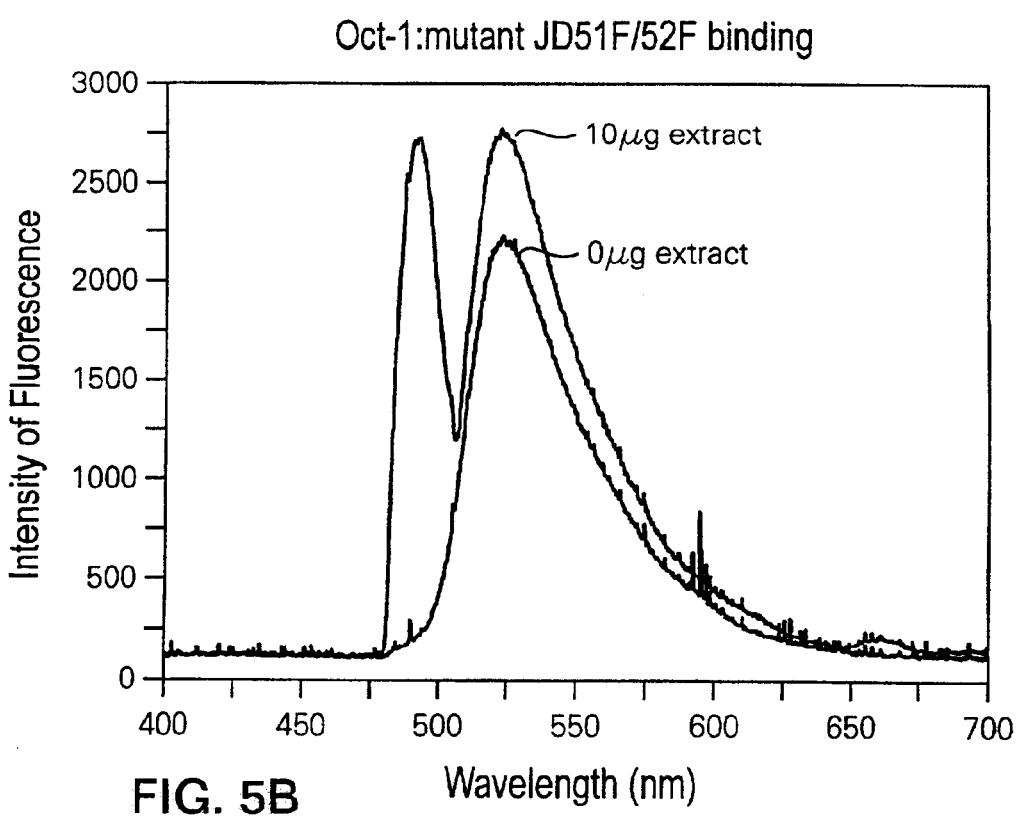

The fluorescent spectra obtained when 10 μg of HeLa cell nuclear extract was reacted with 0.05 pmole wild-type JD49F/50F or 0.05 pmole mutant JD51F/52F are shown in FIGS. 5A and 5B, respectively. The Oct-1 protein present in the HeLa cell nuclear extract, bound specifically to the wild-type high affinity Oct-1 binding site, resulting in a 22% decrease in fluorescent intensity compared to the level observed with JD49F/50F alone (FIG. 5A). By contrast, Oct-1 did not bind to mutant JD51F/52F, as indicated by the increase in fluorescent intensity above that observed with mutant DNA alone (FIG. 5B), confirming the sequence specificity of the assay. These experiments demonstrated the specific detection of another completely different class of DNA-binding proteins.

Moreover, this example confirmed that specific protein:DNA binding may be reliably measured by the invention even when using crude HeLa cell nuclear extracts, that contain hundreds of other DNA-binding proteins. Specificity is conferred by the selection of the appropriately labeled DNA sequence, that recognizes the particular DNA-binding protein to be studied.

Example 6

This Example clearly demonstrates that the method of the invention can measure binding of a multi-protein complex (consisting of two or more different proteins) to one (or more) binding sites on a DNA sequence. Studies were conducted on the binding of the human cellular proteins octamer-binding protein (Oct-1) and host cellular factor (HCF—see, e.g., Wilson et al., "The VP16 accessory protein HCF is a family of polypeptides processed from a large precursor protein." 74 Cell 115–125 (1993)) with the herpes simplex virus type 1 (HSV-1) protein VP16 (or Vmw65) to the DNA sequence TAATGARAT (where R is a purine). This multi-protein:DNA complex is called the immediate early complex (IEC) or VP16-induced complex. Although VP16 is the most potent trans-activator of genes ever identified, it cannot bind DNA efficiently on its own. Instead, it interacts specifically with Oct-1 and HCF to induce genes. VP16 binds to Oct-1 and HCF via its amino terminal 411 amino acids. The C-terminal highly acidic domain of VP16, defined by amino acids 411 to 490, functions as the potent transcriptional activating region. See, e.g., Dalrymple et al., "DNA sequence of the herpes simplex virus type 1 gene whose product is responsible for transcriptional activation of immediate early promoters." 13 Nucleic Acids Research 7865–7879 (1985).

Oct-1 binds to DNA via its bipartite POU domain, which is capable of displaying exceptional DNA sequence recognition flexibility. The Oct-1 POU domain binds to the octamer sequence ATGCAAAT as a monomer, with the $POU_S$ domain contacting the 5' half of this site (ATGC) and the $POU_H$ domain interacting with the 3' half of this site (AAAT) on opposite sides of the DNA. When Oct-1 is bound to the high affinity ATGCAAAT binding site, it is incapable of interacting with VP16.

Oct-1 also binds to DNA sites that bear little resemblance to the octamer consensus. For example, Oct-1 by itself or in association with HCF and VP16 can bind the DNA sequence TAATGARAT, which bears as little as a 4 of 8 bp match to the octamer consensus site. Two forms of the TAATGARAT site are found in the promoter sequences of the herpes simplex virus immediate early (HSV IE) genes. The first, designated the (OCTA$^+$)TAATGARAT motif, contains an overlapping octamer/TAATGARAT sequence, which binds Oct-1 with high affinity. The second, called (OCTA$^-$) TAATGARAT, lacks an overlapping octamer sequence and binds Oct-1 with relatively low affinity. The $POU_H$ domain of Oct-1 binds the 5' TAAT sequence, while the $POU_S$ domain binds the GARAT sequence on the (OCTA$^-$) TAATGARAT site. On the (OCTA$^+$)TAATGARAT binding site, the $POU_H$ domain remains fixed to the TAAT sequence, while the $POU_S$ domain can bind either the 5' ATGC sequence or the 3' GARAT element. The Oct-1 $POU_H$ domain is sufficient for interacting with VP16.

The HCF is required to stabilize the association of Oct-1 with VP16 on a TAATGARAT site, by first forming a stable complex with VP16 independent of Oct-1 or the TAATGARAT element. The exact mechanism by which HCF stabilizes VP16 association with Oct-1 is unknown. The HCF may induce a conformational change within VP16, which primes VP16 to interact with Oct-1 and the GARAT element of the TAATGARAT site. Alternatively, within the IEC complex, the HCF may contact Oct-1 or the DNA, and thus confer greater stability to the complex.

A wild-type fluorescein labeled dsDNA oligonucleotide, JD41F/42F, containing an (OCTA$^-$) TAATGARAT site was derived from a 20 bp region (−343 to −324) from the HSV-1 IE gene 4/5 promoter. Complementary 5'-fluorescein labeled ssDNA 20-mers JD41F and JD42F were synthesized, purified and annealed as above.

```
Sequence for wild-type JD41F (SEQ ID NO:15):
5'-Flu-GGC GGT AAT GAG ATA CGA GC-3'

Sequence for wild-type JD42F (SEQ ID NO:16):
5'-Flu-GCT CGT ATC TCA TTA CCG CC-3'
```

Mutant dsDNA 20-mer JD43F/44F was identical in sequence to wild-type JD41F/42F, except for a double point mutation ($A_2A_3$ CC) (underlined) that inactivated the $POU_H$ binding site, and a second double point mutation ($A_8T_9$ CG) (underlined) that inactivated the $POU_S$ binding site, thereby converting the Oct-1 binding site TAATGAGAT to TCCTGAGCG.

```
Sequence for mutant JD43F (SEQ ID NO:17):
5'-Flu-GGC GGT CCT GAG CGA CGA GC-3'

Sequence for mutant JD44F (SEQ ID NO:18):
5'-Flu-GCT CGT CGC TCA GGA CCG CC-3'
```

A wild-type fluorescein labeled dsDNA oligonucleotide, JD45F/46F, containing a (OCTA$^+$)TAATGARAT site was derived from a 23 bp region (−170 to −148) from the HSV-1 IE gene 1 promoter. Complementary 5'-fluorescein labeled ssDNA 23-mers JD45F and JD46F were synthesized, purified and annealed as above.

```
Sequence for wild-type JD45F (SEQ ID NO:19):
5'-Flu-GTG CAT GCT AAT GAT ATT CTT TG-3'

Sequence for wild-type JD46F (SEQ ID NO:20):
5'-Flu-CAA AGA ATA TCA TTA GCA TGC AC-3'
```

Mutant dsDNA 23-mer JD47F/48F was identical in sequence to wild-type JD45F/46F, except for a double point mutation ($A_6A_7$ CC) (underlined) that inactivated the $POU_H$ binding site, and two additional double point mutations ($A_1T_2$ CG) and ($A_{12}T_{13}$ CG) (underlined) that inactivated the two $POU_S$ binding sites, thereby converting the Oct-1 binding site ATGCTAATGATAT to CGGCTCCTGATCG.

```
Sequence for mutant JD47F (SEQ ID NO:21):
5'-Flu-GTG CCG GCT CCT GAT CGT CTT TG-3'

Sequence for mutant JD48F (SEQ ID NO:22):
5'-Flu-CAA AGA CGA TCA GGA GCC GGC AC-3'
```

The Oct-1:HCF:VP16:DNA binding reaction mixture (30 μl) contained the following: 9.25 mM HEPES, pH 7.9, 2.23 mM $MgCl_2$, 0.03 mM EDTA, 63 mM NaCl, 1.0 mM DTT, 3.75% (v/v) glycerol, 0.10 mg/ml BSA, 0.01 mM PMSF, 133 μg/ml poly(dI)-poly(dC), 67 μg/ml poly(dG-dC)-poly(dG-dC), 0–25 μg HeLa cell nuclear extract (Promega), 0–0.1 μg HSV-1 virion extract and 0.025 pmole 5'-fluorescein labeled dsDNA oligonucleotide. The HSV-1 virion extract containing 80% pure VP16 was kindly provided by Dr. Chris Preston (MRC Institute of Virology, Glasgow, Scotland). HeLa cell nuclear extracts served as the source for Oct-1 and HCF. All components except the DNA and the virion extract were incubated at 21° C. for 10 minutes. DNA was then added, followed by the addition of HSV-1 virion extract (where appropriate). Reaction mixtures were incubated for an additional 30 minutes at 21° C., placed into a quartz cuvette, irradiated with an argon ion laser beam having a wavelength of 488 nm and monitored for fluorescent emission.

Figure 6A:
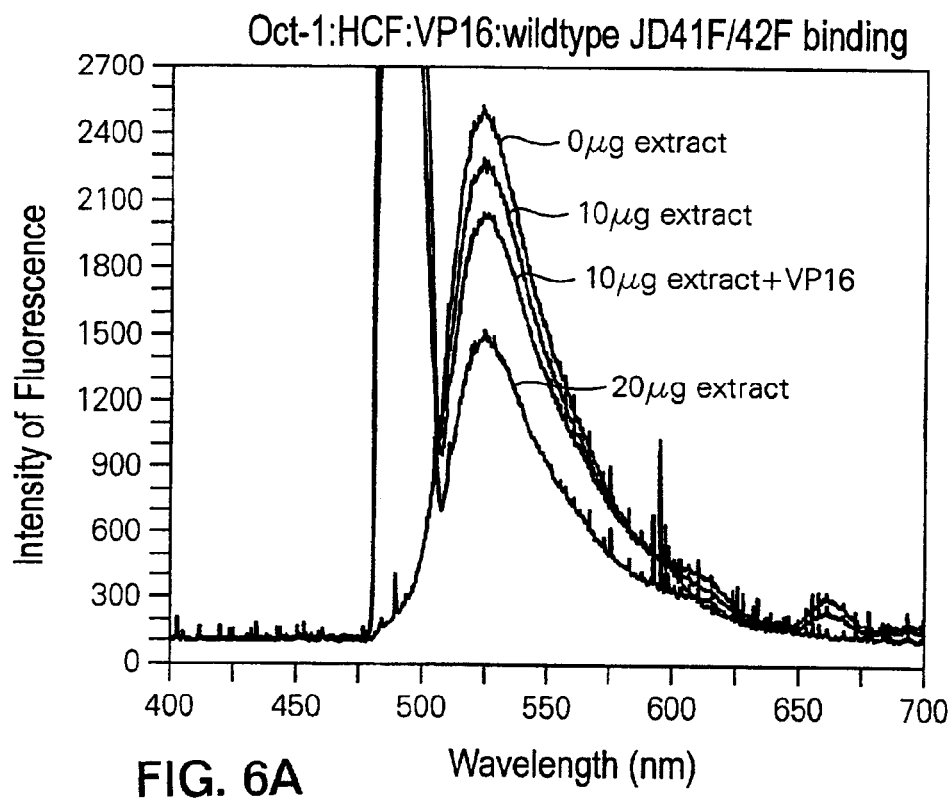

The Oct-1 protein, present in 10 μg and 20 μg of HeLa cell nuclear extract, bound specifically to 0.025 pmole wild-type JD41F/42F, resulting in a 10% and a 43% decrease, respectively, in fluorescent intensity compared to the level achieved with JD41F/42F alone (FIG. 6A). The low DNA amount of 0.025 pmole was in molar excess to the amount of Oct-1 present in the HeLa cell nuclear extract. The observation that 10 μg of HeLa cell nuclear extract produced a 22% decrease in fluorescent intensity when Oct-1 was bound to 0.05 pmole of its high affinity JD49F/50F binding site (in Example 5), whereas the same amount of HeLa cell nuclear extract resulted in only a 10% decrease in fluorescent intensity when Oct-1 was bound to 0.025 pmole of its low affinity JD41F/42F binding site (which is in molar excess to the amount of Oct-1 present), verified the ability of the laser binding assay to discriminate between high affinity and low affinity DNA binding sites for the same protein.

When 0.1 μg of VP16 was added to the Oct-1:JD41F/42F reaction mix, a 20% decrease in fluorescent intensity was observed, representing a further decrease of 10% from the level achieved from the Oct-1:JD41F//42F complex alone (FIG. 6A). This additional decrease arose from the multi-protein Oct-1:HCF:VP16:JD41F/42F complex formation, which was able to absorb and retain more emitted fluorescent light than the single protein Oct-1:JD41F/42F complex.

Figure 6B:
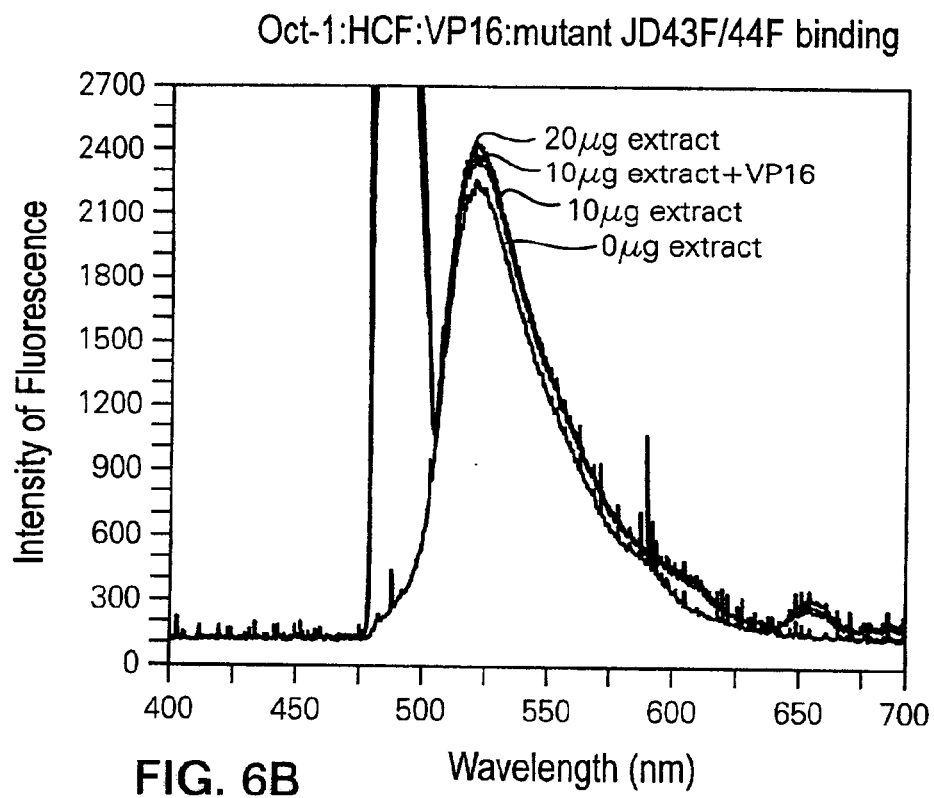

No decrease in fluorescent intensity was observed when 10 μg or 20 μg of HeLa cell nuclear extract, in the absence or presence of VP16, was reacted with 0.025 pmole mutant JD43F/44F, indicating non-binding of Oct-1 or Oct-1:HCF:VP16 complex to the mutated DNA sequence (FIG. 6B). These mutant DNA binding studies confirmed the specificity of the laser detection method for measuring specific multi-protein:DNA complex formation using crude nuclear extracts.

Figure 7A:
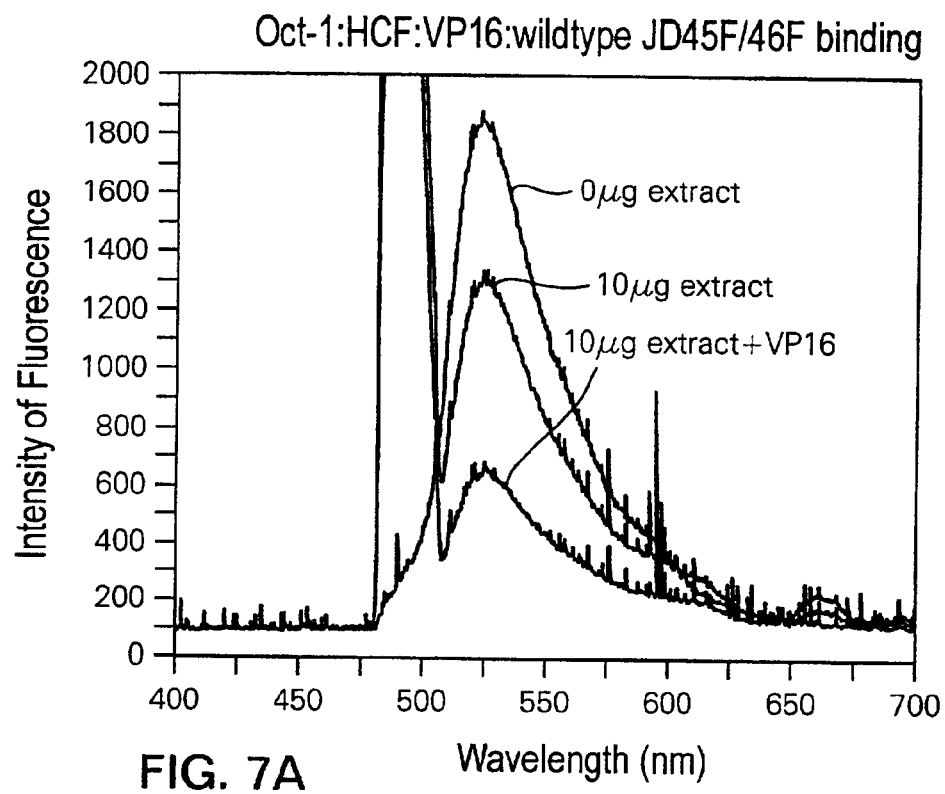

When 10 μg of HeLa cell nuclear extract was reacted with 0.025 pmole of wild-type JD45F/46F, a 32% decrease in fluorescent intensity occurred, compared to the fluorescent intensity observed with JD45F/46F alone (FIG. 7A). This relatively large decrease in intensity is a function of Oct-1's ability to bind with high affinity to the (OCTA$^+$) TAATGARAT site.

Addition of 0.1 μg of VP16 to 10 μg HeLa cell nuclear extract and 0.025 pmole wild-type JD45F/46F, resulted in a 69% decrease in fluorescent intensity, representing a further decrease of 37% from the intensity level obtained from the Oct-1:JD45F/46F complex alone (FIG. 7A). Since Oct-1, HCF and VP16 are 110 KDa, ~300 KDa and 65 KDa in size, respectively, the huge 69% decrease is a direct result of highly efficient multi-protein Oct-1:HCF:VP16 binding to the (OCTA$^+$)TAATGARAT site present in JD45F/46F.

Figure 7B:
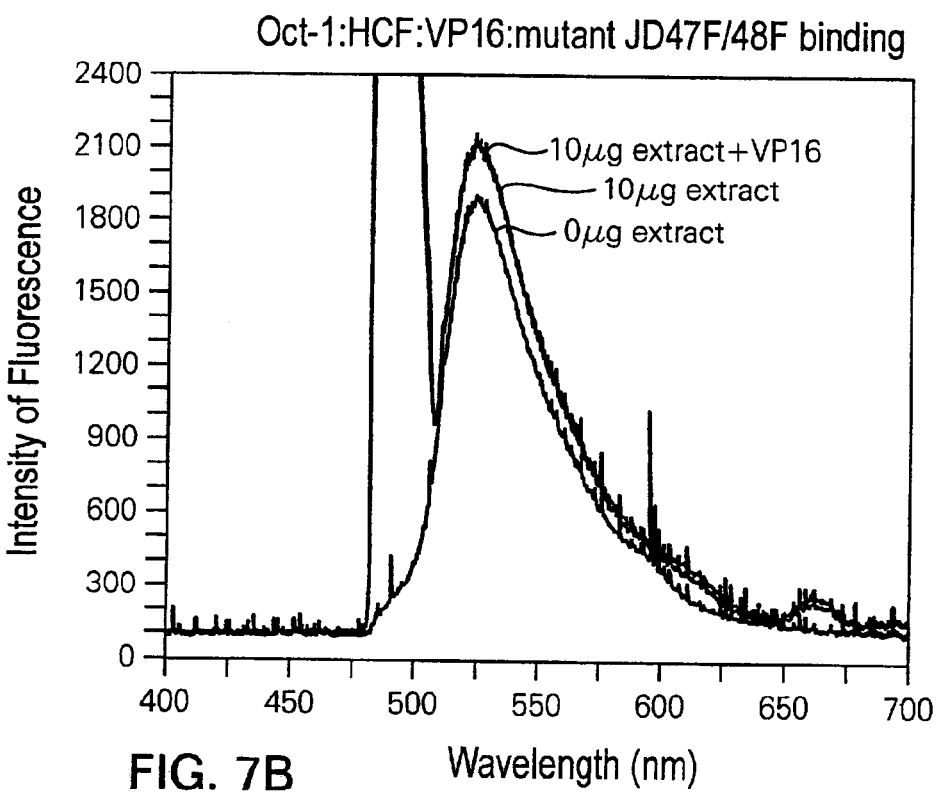

By contrast, no decrease in fluorescent intensity was observed when 10 μg of HeLa cell nuclear extract, in the absence or presence of 0.1 μg VP16, was reacted with 0.025 pmole mutant JD47F/48F (FIG. 7B), clearly indicating disruption of DNA binding to the mutated DNA sequence, and further proving the specificity of the laser binding assay.

This example clearly demonstrates that the method of the invention can reproducibly measure specific binding of a multi-protein complex (consisting of two or more different proteins) to one (or more) binding sites on a DNA sequence, when using crude nuclear cell extracts. Furthermore, the laser binding assay can evaluate the affinity of a specific protein or multi-protein complex to any given DNA sequence.

As demonstrated by the Examples, the invention is applicable to all classes of DNA-binding proteins. For example, when the oncoprotein c-JUN binds to its specific DNA recognition site, a 55% decrease in measurable units is observed, compared to the level achieved by unbound DNA (FIGS. 1A and 1B). No decrease is observed when c-JUN is reacted with a mutant DNA sequence (FIGS. 1C and 1D), indicating non-binding and confirming the specificity of the detection method.

Furthermore, specific binding of peptides containing just the DNA-binding domain of the protein can be detected in a quantitative manner. For example, 20 ng, 100 ng and 200 ng of c-JUN peptide bound to wild-type DNA results in 13%, 28% and 43% decreases, respectively, compared to the level observed for free DNA (FIG. 2A). The fact that the binding of just 20 ng of c-JUN peptide can be reliably measured, demonstrates the high sensitivity of the detection assay. By contrast, 20 ng, 100 ng and 200 ng of c-JUN peptide do not bind mutant DNA, resulting in minor increases above the level observed with mutant DNA alone (FIG. 2B). Binding of peptides in lieu of full length proteins may be of particular interest to designing and/or screening pharmaceuticals.

Figure 3B:
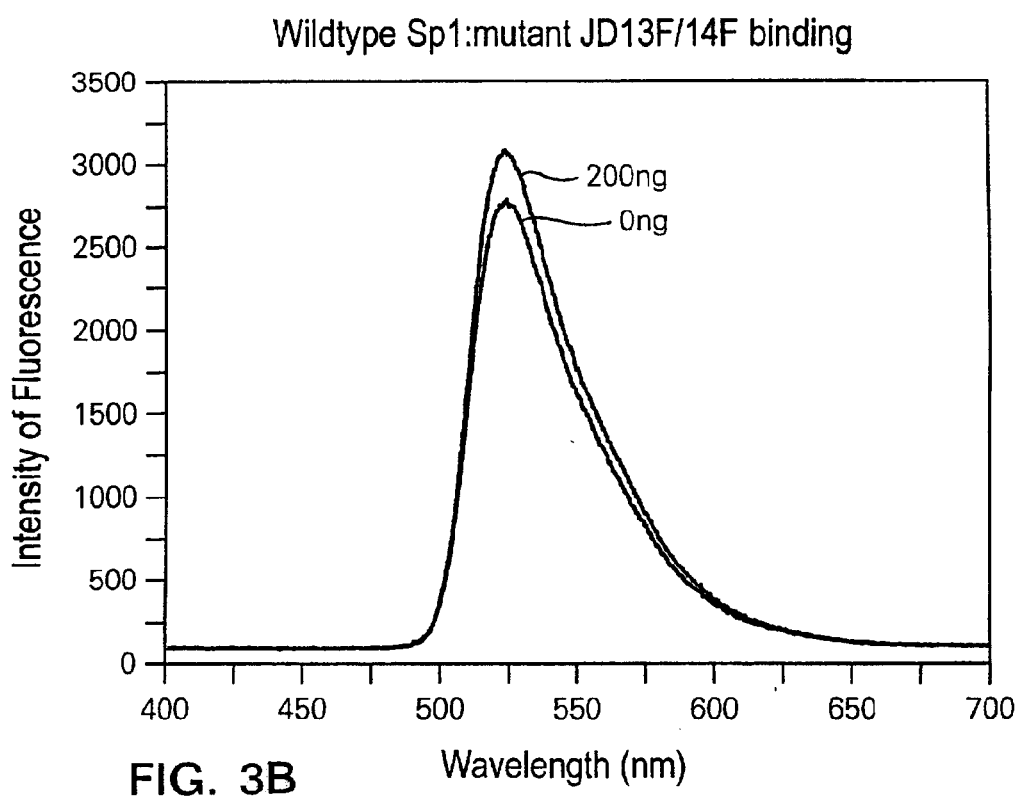

FIGS. 3A and 3B illustrate the binding of the zinc finger DNA-binding protein Sp1 to wild-type or mutant DNA binding sites, respectively. When 200 ng of Sp1 is bound to wild-type DNA, a 44% decrease is observed, compared to the level measured for DNA alone. Non-binding of 200 ng Sp1 is observed for the mutated DNA sequence.

The assay of the invention can differentiate between an antibody:protein:DNA complex and a protein:DNA complex. For example, a 42% and 37% decrease in fluorescent intensity was observed when 5 µg or 1 µg of c-JUN antibody, respectively, was bound to 1 µg c-JUN complexed to wild-type DNA, compared to the 25% decrease obtained for c-JUN:DNA complexes (FIG. 4A). IgG:c-JUN complexes did not bind to mutant DNA sequences.

FIGS. 5, 6 and 7 illustrate the binding of the bipartite POU domain DNA-binding protein Oct-1 to three different DNA sequence recognition sites, with different binding affinities. Moreover, Examples 5 and 6 prove the feasibility of using crude nuclear protein extracts as a source of DNA-binding proteins, while still retaining highly specific protein-DNA binding. Depending on the binding affinity of each DNA site, 10 µg of HeLa cell nuclear extracts bound wild-type Oct-1 DNA binding sites with a 10%, 22% or 32% decrease, compared to levels achieved for unbound DNA.

Significantly, the method of the invention can reliably measure the binding of multi-protein complexes (consisting of two or more different proteins) to one (or more) DNA binding sites, whether pure proteins or crude nuclear extracts are used. For example, Oct-1:HCF:VP16:DNA complexes yielded a 69% and 20% decrease in fluorescent intensity when bound to a high affinity (OCTA$^+$)TAATGARAT site or a low affinity (OCTA$^-$)TAATGARAT site, respectively (FIGS. 7 and 6). Non-binding of Oct-1 protein or Oct-1:HCF:VP16 protein complex is observed for all of the mutated DNA sequences.

Multi-protein:DNA complexes are much more prevalent in nature and biologically significant than single protein:DNA complexes. The ability of the method of the invention to employ crude nuclear protein extracts to assay single or multi-protein binding to DNA in a highly specific manner is of major clinical relevance.

While the invention has been described in detail and with reference to specific examples thereof, it will be apparent to one skilled in the art that various changes and modifications can be made therein without departing from the spirit and scope thereof.

What is claimed is:

1. A method for binding a ligand, said method comprising:
providing an aptamer comprising at least two parallel or antiparallel heteropolymeric nucleobase-containing sequences bonded together by Watson-Crick complementary base interaction or by homologous base interaction, wherein: (a) said aptamer comprising a duplex, and said at least two sequences are bonded together by Watson-Crik complememtary base interaction with parallel directionality: (b) said aptamer comprises a duplex, and at least two sequences are bonded together by homologous base interaction with paralleli or antiparallel directionality: (c) said apatmer comprises a triplex, and said at least two sequences are bonded together by Watson-Crik complementary base interaction with parallel or antiparallel directionity: (d) said aptamer comprises a triplex, and said at least two sequences are bonded together by homologeous base interaction with parallel or antiparallel directionality; (e) said aptamer comprises a quadruplex, and said at least two sequences are bonded together by Watson-Crik complementary base interaction with parallel or antiparallel directionality and do not rely on Hoogsteen bonding and GG quartets for maintence of complex structure or (f) said aptamer comprises a quadruplex, and said at least two sequences are bonded together by homologous base interaction with parallel or antiparallel directionality and do not rely on Hoogsteen bonding and GG quartets for maintenance of complex structure; and contacting said aptamer with said ligand to bind said ligand to said aptamer by interaction other than by Watson-Crik base pairing of nucleobase to nucleobase.

2. The method of claim 1, wherein said providing comprises placing said aptamer in solution, on a solid support, in vitro, in vivo or in silico.

3. The method of claim 1, wherein said providing comprises administering said aptamer to an organism.

4. The method of claim 3, wherein said aptamer is administered in an amount effective to alter a biological activity of said ligand.

5. The method of claim 3, wherein said aptamer is labeled and is administered in an amount effective to detect said ligand or said ligand and a second ligand bound to said ligand.

6. The method of claim 1, wherein said providing comprises placing said aptamer in a test medium, and a presence or an absence of said ligand in said test medium is detected.

7. The method of claim 1, wherein said aptamer comprises a duplex, and said at least two sequences are bonded together by Watson-Crick complementary base interaction with parallel directionality.

8. The method of claim 1, wherein said aptamer comprises a duplex, and said at least two sequences are bonded together by homologous base interaction with parallel or antiparallel directionality.

9. The method of claim 1, wherein said aptamer comprises a triplex, and said at least two sequences are bonded together by Watson-Crick complementary base interaction with parallel or antiparallel directionality.

10. The method of claim 1, wherein said aptamer comprises a triplex, and said at least two sequences are bonded together by homologous base interaction with parallel or antiparallel directionality.

11. The method of claim 1, wherein said aptamer comprises a quadruplex, and said at least two sequences are bonded together by Watson-Crick complementary base interaction with parallel or antiparallel directionality.

12. The method of claim 1, wherein said aptamer comprises a quadruplex, and said at least two sequences are bonded together by homologous base interaction with parallel or antiparallel directionality.

13. The method of claim 1, wherein said ligand comprises a protein or peptide.

14. The method of claim 1, wherein said ligand is free of nucleobases.

15. The method of claim 1, wherein some nucleobases in said at least two sequences are not paired.

16. The method of claim 1, wherein said at least two sequences are contained in at least two nucleic acid strands that are cross-linked.

17. The method of claim 1, wherein the aptamer is an aptazyme.

* * * * *

UNITED STATES PATENT AND TRADEMARK OFFICE
CERTIFICATE OF CORRECTION

PATENT NO.    : 6,858,390 B2
DATED         : February 22, 2005
INVENTOR(S)   : Glen H. Erikson et al.

It is certified that error appears in the above-identified patent and that said Letters Patent is hereby corrected as shown below:

Column 5,
Line 8, "condsidered" should read -- considered --.

Column 31,
Line 7, "comprising" should read -- comprises --;
Lines 9, 15, 22 and 33, each occurrence of "Crik" should read -- Crick --;
Line 10, "directionality:" should read -- directionality; --
Line 13, "directionality:" should read -- directionality; -- and "apatmer" should read -- aptamer --;
Line 16, "directionity:" should read -- directionality; --;
Line 18, "homologeous" should read -- homologous --; and
Line 24, "maintence" should read -- maintenance --.

Signed and Sealed this

Seventeenth Day of May, 2005

JON W. DUDAS
*Director of the United States Patent and Trademark Office*